United States Patent
Xia et al.

(10) Patent No.: US 8,586,204 B2
(45) Date of Patent: Nov. 19, 2013

(54) PHOSPHORESCENT EMITTERS AND HOST MATERIALS WITH IMPROVED STABILITY

(75) Inventors: Chuanjun Xia, Lawrenceville, NJ (US); Walter Yeager, Yardley, PA (US); Bin Ma, West Windsor, NJ (US); Scott Beers, Flemington, NJ (US); Jui-Yi Tsai, Lawrenceville, NJ (US); James Fiordeliso, Morrisville, PA (US); Edward Barron, Hamilton, NJ (US); Chun Lin, Langhorne, PA (US)

(73) Assignee: Universal Display Corporation, Ewing, NJ (US)

( * ) Notice: Subject to any disclaimer, the term of this patent is extended or adjusted under 35 U.S.C. 154(b) by 453 days.

(21) Appl. No.: 12/869,284

(22) Filed: Aug. 26, 2010

(65) Prior Publication Data

US 2011/0057559 A1 Mar. 10, 2011

Related U.S. Application Data

(63) Continuation-in-part of application No. 12/208,907, filed on Sep. 11, 2008, now Pat. No. 8,007,927.

(60) Provisional application No. 61/239,932, filed on Sep. 4, 2009, provisional application No. 61/017,480, filed on Dec. 28, 2007.

(51) Int. Cl.
   *H01L 51/54* (2006.01)
   *C09K 11/06* (2006.01)

(52) U.S. Cl.
   USPC ........... 428/690; 428/917; 313/504; 313/506; 257/E51.044; 257/E51.05

(58) Field of Classification Search
   None
   See application file for complete search history.

(56) References Cited

U.S. PATENT DOCUMENTS

| | | | |
|---|---|---|---|
| 4,769,292 A | 9/1988 | Tang et al. | |
| 5,061,569 A | 10/1991 | VanSlyke et al. | |
| 5,247,190 A | 9/1993 | Friend et al. | |
| 5,703,436 A | 12/1997 | Forrest et al. | |
| 5,707,745 A | 1/1998 | Forrest et al. | |
| 5,834,893 A | 11/1998 | Bulovic et al. | |
| 5,884,363 A | 3/1999 | Tofts | |
| 6,013,982 A | 1/2000 | Thompson et al. | |
| 6,091,195 A | 7/2000 | Forrest et al. | |
| 6,097,147 A | 8/2000 | Baldo et al. | |
| 6,294,398 B1 | 9/2001 | Kim et al. | |
| 6,303,238 B1 | 10/2001 | Thompson et al. | |
| 6,337,102 B1 | 1/2002 | Forrest et al. | |
| 6,468,819 B1 | 10/2002 | Kim et al. | |
| 6,687,266 B1 | 2/2004 | Ma et al. | |
| 6,835,469 B2 | 12/2004 | Kwong et al. | |
| 7,087,321 B2 | 8/2006 | Kwong et al. | |
| 7,279,704 B2 | 10/2007 | Walters et al. | |
| 7,431,968 B1 | 10/2008 | Shtein et al. | |
| 2002/0034656 A1 | 3/2002 | Thompson et al. | |
| 2002/0134984 A1 | 9/2002 | Igarashi | |
| 2003/0175553 A1 | 9/2003 | Thompson et al. | |
| 2003/0230980 A1 | 12/2003 | Forrest et al. | |
| 2004/0174116 A1 | 9/2004 | Lu et al. | |
| 2005/0025993 A1 | 2/2005 | Thompson et al. | |
| 2005/0260441 A1 | 11/2005 | Thompson et al. | |
| 2005/0260449 A1 | 11/2005 | Walters et al. | |
| 2006/0008670 A1 | 1/2006 | Lin et al. | |
| 2006/0197077 A1 | 9/2006 | Okuda et al. | |
| 2006/0202194 A1 | 9/2006 | Jeong et al. | |
| 2006/0251923 A1 | 11/2006 | Lin et al. | |
| 2007/0088167 A1 | 4/2007 | Lin et al. | |
| 2007/0190359 A1 | 8/2007 | Knowles et al. | |
| 2009/0167162 A1 | 7/2009 | Lin et al. | |
| 2009/0200927 A1 | 8/2009 | D'Andrade et al. | |
| 2010/0045172 A1* | 2/2010 | Hiyama et al. ................ 313/504 |

FOREIGN PATENT DOCUMENTS

| | | |
|---|---|---|
| EP | 0650955 | 5/1995 |
| JP | 2003109758 | 4/2003 |
| JP | 200511610 | 1/2005 |
| JP | 2007123392 | 5/2007 |
| JP | 2007254297 | 10/2007 |
| JP | 2008147354 | 6/2008 |
| JP | 2009-114369 A * | 5/2009 |
| WO | WO 01/39234 | 5/2001 |
| WO | WO 02/02714 | 1/2002 |
| WO | WO 03/040257 | 5/2003 |
| WO | WO 03/060956 | 7/2003 |
| WO | WO 2004093207 | 10/2004 |
| WO | WO 2004107822 | 12/2004 |
| WO | WO 2005014551 | 2/2005 |
| WO | WO 2005030900 | 4/2005 |
| WO | WO 2005089025 | 9/2005 |
| WO | WO 2005123873 | 12/2005 |
| WO | WO 2006009024 | 1/2006 |
| WO | WO 2006056418 | 6/2006 |

(Continued)

OTHER PUBLICATIONS

Machine translation of JP 2008-147354 A (Jun. 2008).*
Machine translation of JP 2009-114369 A (May 2009).*
Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino)triphenylamine (m-MTDATA), as Hole-Transport Materials," *Adv. Mater.*, 6(9):677-679 (1994).

(Continued)

*Primary Examiner* — Marie R. Yamnitzky
(74) *Attorney, Agent, or Firm* — Duane Morris LLP

(57) ABSTRACT

Devices containing a particular combination of organic compounds are provided. In particular, the devices contain twisted aryl compounds having extended conjugation (i.e., the twisted aryl is substituted with an additional aryl group) in combination with dibenzothiophene or dibenzofuran containing host materials. The organic light emitting devices may provide improved stability color, lifetime and manufacturing. Compounds containing a twisted aryl having extended conjugation are also provided.

4 Claims, 4 Drawing Sheets

(56) References Cited

FOREIGN PATENT DOCUMENTS

| WO | WO 2006082742 | | 8/2006 |
| WO | WO 2006098120 | | 9/2006 |
| WO | WO 2006103874 | | 10/2006 |
| WO | WO 2006114966 | | 11/2006 |
| WO | WO 2006121811 | | 11/2006 |
| WO | WO 2006132173 | | 12/2006 |
| WO | WO 2007004380 | | 1/2007 |
| WO | WO 2007063754 | | 6/2007 |
| WO | WO 2007063796 | | 6/2007 |
| WO | WO 2007108362 | | 9/2007 |
| WO | WO 2007108459 | | 9/2007 |
| WO | WO 2008/120611 | A1 * | 10/2008 |
| WO | WO 2009030981 | | 3/2009 |

OTHER PUBLICATIONS

Paulose, Betty Marie Jennifer S. et al., "First Examples of Alkenyl Pyridines as Organic Ligands for Phosphorescent Iridium Complexes," *Adv. Mater.*, 16(22):2003-2007 (2004).

Tung, Yung-Liang et al., "Organic Light-Emitting Diodes Based on Charge-Neutral Ru$^{II}$ PHosphorescent Emitters," Adv. Mater., 17(8):1059-1064 (2005).

Huang, Jinsong et al., "Highly Efficient Red-Emission Polymer Phosphorescent Light-Emitting Diodes Based on Two Novel Tris(1-phenylisoquinolinato-C2,N)iridium(III) Derivatives," *Adv. Mater.*, 19:739-743 (2007).

Wong, Wai-Yeung, "Multifunctional Iridium Complexes Based on Carbazole Modules as Highly Efficient Electrophosphors," *Angew. Chem. Int. Ed.*, 45:7800-7803 (2006).

Tang, C.W. and VanSLYKE, S.A., "Organic Electroluminescent Diodes," *Appl. Phys. Lett.*, 51(12):913-915 (1987).

Adachi, Chihaya et al., "Organic Electroluminescent Device Having a Hole Conductor as an Emitting Layer," *Appl. Phys. Lett.*, 55(15):1489-1491 (1989).

Ma, Yuguang et al., "Triplet Luminescent Dinuclear-Gold(/) Complex-Based Light-Emitting Diodes with Low Turn-On voltage," *Appl. Phys. Lett.*, 74(10):1361-1363 (1999).

Gao, Zhiqiang et al., "Bright-Blue Electroluminescence From a Silyl-Substituted ter-(phenylene-vinylene) derivative," *Appl. Phys. Lett.*, 74(6):865- 867 (1999).

Baldo, M.A. et al., "Very High-Efficiency Green Organic Light-Emitting Devices Based on Electrophosphorescence," *Appl. Phys. Lett.*, 75(1):4-6 (1999).

Lee, Chang-Lyoul et al., "Polymer Phosphorescent Light-Emitting Devices Doped with Tris(2-phenylpyridine) Iridium as a Triplet Emitter," *Appl. Phys. Lett.*, 77(15):2280-2282 (2000).

Hung, L.S. et al., "Anode Modification in Organic Light-Emitting Diodes by Low-Frequency Plasma Polymerization of $CHF_3$," *Appl. Phys. Lett.*, 78(5):673-675 (2001).

Ikai, Masamichi and Tokito, Shizuo, "Highly Efficient Phosphorescence From Organic Light-Emitting Devices with an Exciton-Block Layer," *Appl. Phys. Lett.*, 79(2):156-158 (2001).

Wang, Y. et al., "Highly Efficient Electroluminescent Materials Based on Fluorinated Organometallic Iridium Compounds," *Appl. Phys. Lett.*, 79(4):449-451 (2001).

Kwong, Raymond C. et al., "High Operational Stability of Electrophosphorescent Devices," *Appl. Phys. Lett.*, 81(1):162-164 (2002).

Holmes, R.J. et al., "Blue Organic Electrophosphorescence Using Exothermic Host-Guest Energy Transfer," *Appl. Phys. Lett.*, 82(15):2422-2424 (2003).

Sotoyama, Wataru et al., "Efficient Organic Light-Emitting Diodes with Phosphorescent Platinum Complexes Containing N^C^N-Coordinating Tridentate Ligand," *Appl. Phys. Lett.*, 86:153505-1-153505-3 (2005).

Okumoto, Kenji et al., "Green Fluorescent Organic Light-Emitting Device with External Quantum Efficiency of Nearly 10%," *Appl. Phys. Lett.*, 89:063504-1-063504-3 (2006).

Kanno, Hiroshi et al., "Highly Efficient and Stable Red Phosphorescent Organic Light-Emitting Device Using bis[2-(2-benzothiazoyl)phenolato]zinc(II) as host material," *Appl. Phys. Lett.*, 90:123509-1-123509-3 (2007).

Aonuma, Masaki et al., "Material Design of Hole Transport Materials Capable of Thick-Film Formation in Organic Light Emitting Diodes," *Appl. Phys. Lett*, 90:183503-1-183503-3 (2007).

Sun, Yiru and Forrest, Stephen R., "High-Efficiency White Organic Light Emitting Devices with Three Separate Phosphorescent Emission Layers," *Appl. Phys. Lett.*, 91:263503-1-263503-3 (2007).

Adachi, Chihaya et al., "High-Efficiency Red Electrophosphorescence Devices," *Appl. Phys. Lett.*, 78(11):1622-1624 (2001).

Wong, Keith Man-Chung et al.,"A Novel Class of Phosphorescent Gold(III) Alkynyl-Based Organic Light-Emitting Devices with Tunable Colour," *Chem. Commun.*, 2906-2908 (2005).

Hamada, Yuji et al., "High Luminance in Organic Electroluminescent Devices with Bis(10-hydroxybenzo[h]quinolinato)beryllium as an Emitter," *Chem. Lett.*, 905-906 (1993).

Nishida, Jun-ichi et al., "Preparation, Characterization, and Electroluminescence Characteristics of α-Diimine-type Platinum(II) Complexes with Perfluorinated Phenyl Groups as Ligands," *Chem. Lett.*, 34(4):592-593 (2005).

Mi, Bao-Xiu et al., "Thermally Stable Hole-Transporting Material for Organic Light-Emitting Diode: an Isoindole Derivative," *Chem. Mater.*, 15(16):3148-3151 (2003).

Huang, Wei-Sheng et al., "Highly Phosphorescent Bis-Cyclometalated Iridium Complexes Containing Benzoimidazole-Based Ligands," *Chem. Mater.*, 16(12):2480-2488 (2004).

Niu, Yu-Hua et al., "Highly Efficient Electrophosphorescent Devices with Saturated Red Emission from a Neutral Osmium Complex," *Chem. Mater.*, 17(13):3532-3536 (2005).

Lo, Shih-Chun et al., "Blue Phosphorescence from Iridium(III) Complexes at Room Temperature," *Chem. Mater.*, 18(21):5119-5129 (2006).

Takizawa, Shin-ya et al., "Phosphorescent Iridium Complexes Based on 2-Phenylimidazo[1,2- α]pyridine Ligands: Tuning of Emission Color toward the Blue Region and Application to Polymer Light-Emitting Devices," *Inorg. Chem.*, 46(10):4308-4319 (2007).

Lamansky, Sergey et al., "Synthesis and Characterization of Phosphorescent Cyclometalated Iridium Complexes," *Inorg. Chem.*, 40(7):1704-1711 (2001).

Ranjan, Sudhir et al., "Realizing Green Phosphorescent Light-Emitting Materials from Rhenium(I) Pyrazolato Diimine Complexes," *Inorg. Chem.*, 42(4):1248-1255 (2003).

Noda, Tetsuya and Shirota,Yasuhiko, "5,5'-Bis(dimesitylboryl)-2,2'-bithiophene and 5,5"-Bis(dimesitylboryl)-2,2':5',2"-terthiophene as a Novel Family of Electron-Transporting Amorphous Molecular Materials," *J. Am. Chem. Soc.*, 120 (37):9714-9715 (1998).

Sakamoto, Youichi et al., "Synthesis, Characterization, and Electron-Transport Property of Perfluorinated Phenylene Dendrimers," *J. Am. Chem. Soc.*, 122(8):1832-1833 (2000).

Adachi, Chihaya et al., "Nearly 100% Internal Phosphorescence Efficiency in an Organic Light Emitting Device," *J. Appl. Phys.*, 90(10):5048-5051 (2001).

Shirota, Yasuhiko et al., "Starburst Molecules Based on π-Electron Systems as Materials for Organic Electroluminescent Devices," *Journal of Luminescence*, 72-74:985-991 (1997).

Inada, Hiroshi and Shirota, Yasuhiko, "1,3,5-Tris[4-(diphenylamino)phenyl]benzene and its Methylsubstituted Derivatives as a Novel Class of Amorphous Molecular Materials," *J. Mater. Chem.*, 3(3):319-320 (1993).

Kido, Junji et al.,"1,2,4-Triazole Derivative as an Electron Transport Layer in Organic Electroluminescent Devices," *Jpn. J. Appl. Phys.*, 32:L917-L920 (1993).

Van Slyke, S. A. et al., "Organic Electroluminescent Devices with Improved Stability," *Appl. Phys. Lett.*, 69(15 ):2160-2162 (1996).

Baldo, M. A. et al., "Highly Efficient Phosphorescent Emission From Organic Electroluminescent Devices," *Nature*, 395:151-154 (1998).

Guo, Tzung-Fang et al., "Highly Efficient Electrophosphorescent Polymer Light-Emitting Devices," *Organic Electronics*, 1:15-20 (2000).

(56) References Cited

OTHER PUBLICATIONS

Palilis, Leonidas C., "High Efficiency Molecular Organic Light-Emitting Diodes Based on Silole Derivatives and Their Exciplexes," *Organic Electronics*, 4:113-121 (2003).

Ikeda, Hisao et al., "P-185: Low-Drive-Voltage OLEDs with a Buffer Layer Having Molybdenum Oxide," *SID Symposium Digest*, 37:923-926 (2006).

T. Östergård et al., "Langmuir-Blodgett Light-Emitting Diodes of Poly(3-Hexylthiophene): Electro-Optical Characteristics Related to Structure," *Synthetic Metals*, 87:171-177 (1997).

Hu, Nan-Xing et al., "Novel High $T_g$ Hole-Transport Molecules Based on Indolo[3,2-*b*]carbazoles for Organic Light-Emitting Devices," *Synthetic Metals*, 111-112:421-424 (2000).

Salbeck, J. et al., "Low Molecular Organic Glasses for Blue Electroluminescence," Synthetic Metals, 91:209-215 (1997).

U.S. Appl. No. 61/094,145, filed Sep. 4, 2008.
U.S. Appl. No. 61/101,757, filed Oct. 1, 2008.
U.S. Appl. No. 61/239,932, filed Sep. 4, 2009.
U.S. Appl. No. 61/017,480, filed Dec. 28, 2007.

* cited by examiner

Compound 1

Compound 2

Compound 3

Compound 5

PHOSPHORESCENT EMITTERS AND HOST MATERIALS WITH IMPROVED STABILITY

This application claims priority to U.S. Provisional Application Ser. No. 61/239,932, filed Sep. 4, 2009, and is a continuation-in-part of U.S. patent application Ser. No. 12/208,907, filed Sep. 11, 2008, now U.S. Pat. No. 8,007,927, which claims priority to U.S. Provisional Application Ser. No. 61/017,480, filed Dec. 28, 2007, the disclosures of which are herein expressly incorporated by reference in its entirety.

The claimed invention was made by, on behalf of, and/or in connection with one or more of the following parties to a joint university corporation research agreement: Regents of the University of Michigan, Princeton University, The University of Southern California, and the Universal Display Corporation. The agreement was in effect on and before the date the claimed invention was made, and the claimed invention was made as a result of activities undertaken within the scope of the agreement.

FIELD OF THE INVENTION

The present invention relates to organic light emitting devices containing a particular combination of organic compounds. More particularly, the invention relates to devices comprising a compound containing a twisted aryl substituent having extended conjugation and a dibenzothiophene and/or dibenzofuran containing compound. The particular combination of organic materials in an OLED may improve device stability, lifetime, efficiency, and sublimation properties.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine) iridium, denoted Ir(ppy)$_3$, which has the structure:

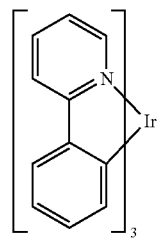

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY OF THE INVENTION

A first device comprising an organic light emitting device is provided. The device further comprising an anode, a cathode; and an organic layer, disposed between the anode and the cathode, the organic layer comprising a first compound itself comprising a ligand having the structure:

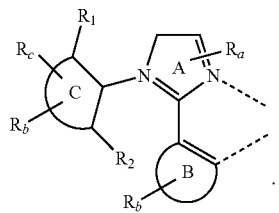

Formula I

B and C are each independently a 5 or 6-membered carbocyclic or heterocyclic ring. A-B and A-C each represent a bonded pair of carbocyclic or heterocyclic rings. Preferably, B is benzene. $R_a$, $R_b$, and $R_c$ may represent mono, di, tri, or tetra substitutions. $R_a$, $R_b$, and $R_c$ are independently selected from the group consisting of hydrogen, halogen, alkyl, alkoxy, amino, alkenyl, alkynyl, arylalkyl, aryl and heteroaryl. $R_1$ and $R_2$ are ortho substituents on ring C. $R_1$ and $R_2$ are independently selected from the group consisting of hydrogen, halogen, alkyl, alkoxy, amino, alkenyl, alkynyl, arylalkyl, aryl and heteroaryl. Preferably, at least one of $R_1$ and $R_2$ is an alkyl. More preferably, at least one of $R_1$ and $R_2$ is an alkyl having two or more carbon atoms. Preferably, each of $R_1$ and $R_2$ is an alkyl. More preferably, each of $R_1$ and $R_2$ is an alkyl having two or more carbon atoms. Ar is a 5 or 6-membered carbocyclic or heterocyclic ring. Preferably, Ar is para to the carbon atom which is bonded to the nitrogen atom in the A ring. Preferably, Ar is benzene. The ligand L is coordinated to a metal M having an atomic number greater than 40. Preferably, M is Ir.

The organic layer comprises a second compound having the formula:

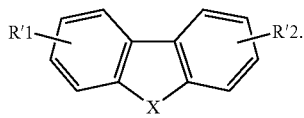

Formula II

X is S or O. $R'_1$ and $R'_2$ are independently selected from the group consisting of hydrogen, alkyl, alkoxy, amino, alkenyl, alkynyl, arylalkyl, aryl and heteroaryl. Preferably, X is S. In one aspect, one of $R'_1$ and $R'_2$ is carbazole. In another aspect, $R'_1$ and $R'_2$ are carbazole.

In one aspect, devices are provided comprising a first compound that has the formula:

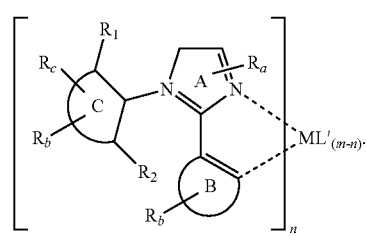

Formula III m is the oxidation state of the metal M. n is at least 1. L' is a monoanionic bidentate ligand.

In another aspect, L' is selected from the group consisting of:

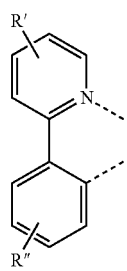

FORMULA IV

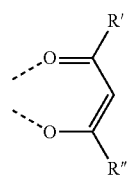

FORMULA V

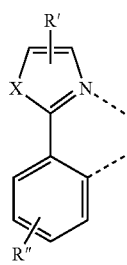

FORMULA VI

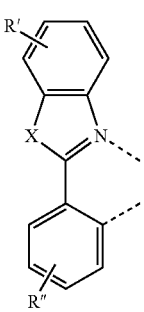

FORMULA VII

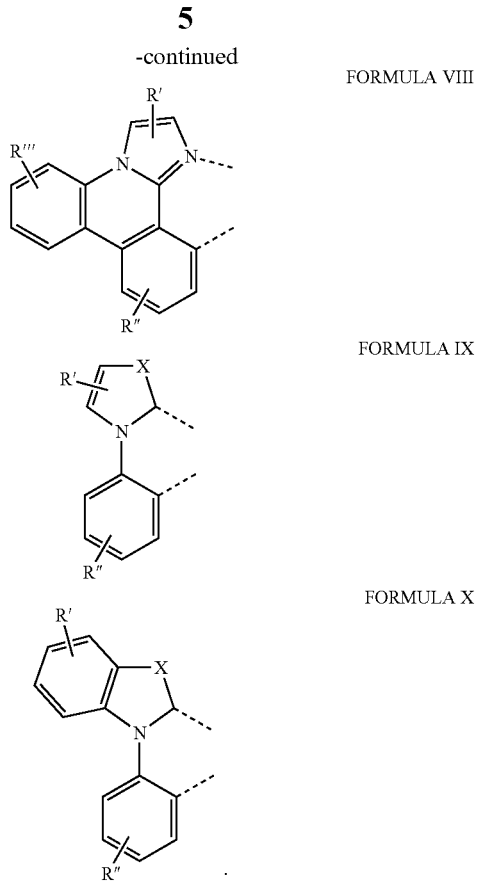

R', R", and R'" are independently selected from the group consisting of hydrogen, halogen, alkyl, alkoxy, amino, alkenyl, alkynyl, arylkyl, arylalkyl, aryl, and heteroaryl. X is selected from the group consisting of S, NZ, O, Se, BZ, CZZ', and C=O. Z and Z' are independently selected from the group consisting of hydrogen, alkyl, and aryl.

Particular devices are provided, wherein the device contains a first compound that is selected from the group consisting of Compound 1-Compound 69.

In one aspect, the first compound is homoleptic. Non-limiting examples of homoleptic compound include Compound 1-Compound 46. In another aspect, the first compound is heteroleptic. Non-limiting examples of heteroleptic compounds include Compound 47-Compound 69.

Specific devices are also provided, wherein the first compound is selected from the group consisting of Compound 1, Compound 2, Compound 3, and Compound 5. Preferably, the device comprises Compound 1 as the first compound.

In one aspect, the organic layer is an emissive layer and the first compound is an emitting dopant and the second compound is a host. In another aspect, the organic layer is an emissive layer comprising a compound having Formula II and at least one of Compounds 1-69 and Formula II is the host material and at least one of Compounds 1-69 is the emitting dopant. Preferably, the organic layer is an emissive layer comprising H1 and at least one of Compound 1, 2, 3, or 5 and H1 is the host material and at least one of Compound 1, 2, 3, or 5 is the emitting dopant. More preferably, Compound 1 is the emitting dopant. Preferably, the organic layer is an emissive layer comprising H2 and Compound 1 and H2 is the host material and Compound 1 is the emitting dopant.

In one aspect, the first device is a display. In another aspect, the first device is an organic light emitting device.

Additionally, compounds comprising a twisted aryl having extended conjugation are provided. The compound is selected from the group consisting of Compound 2-Compound 69. Preferably, the compound is selected from the group consisting of Compound 2-Compound 7.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

Figure 1:
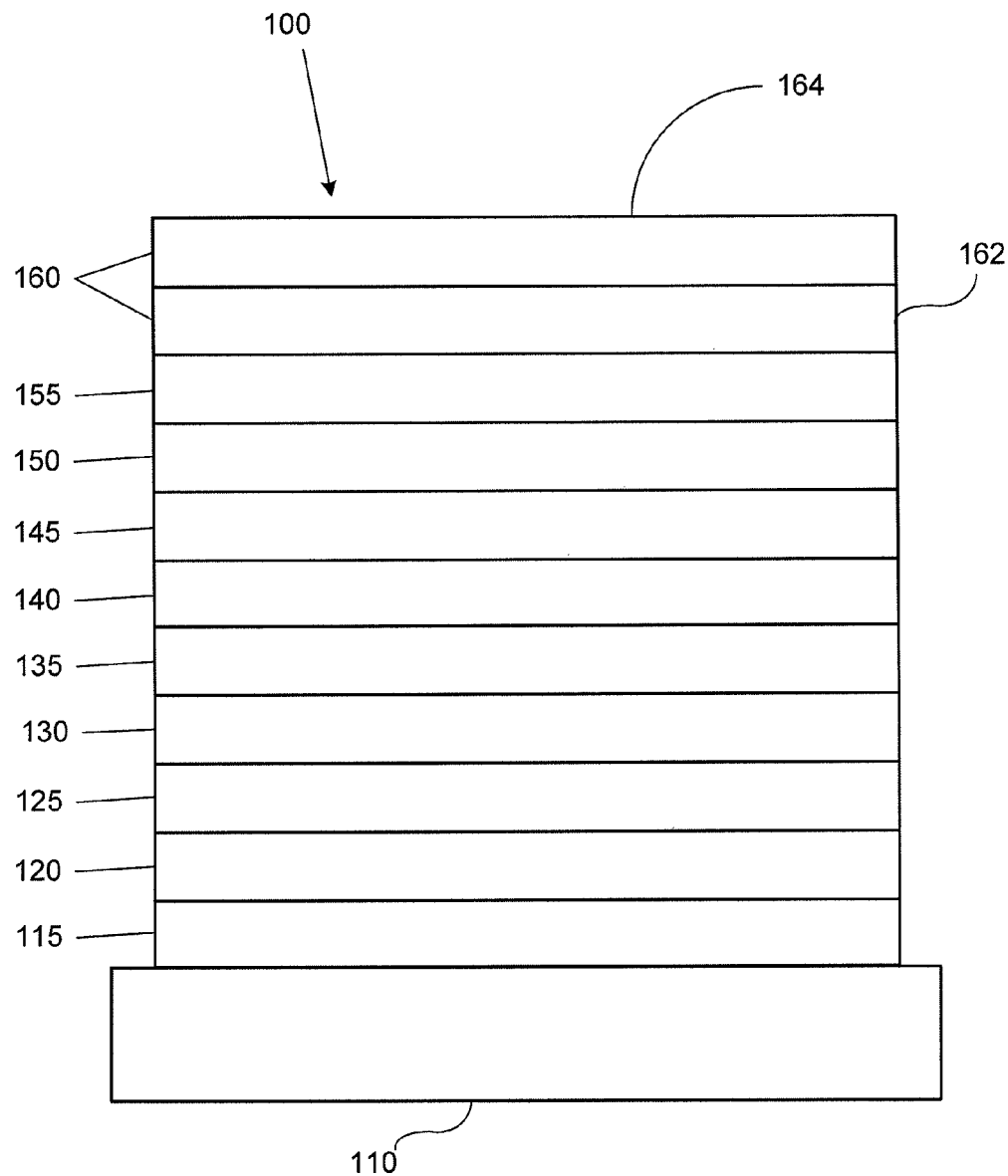
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, and a cathode 160. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with F.sub.4-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
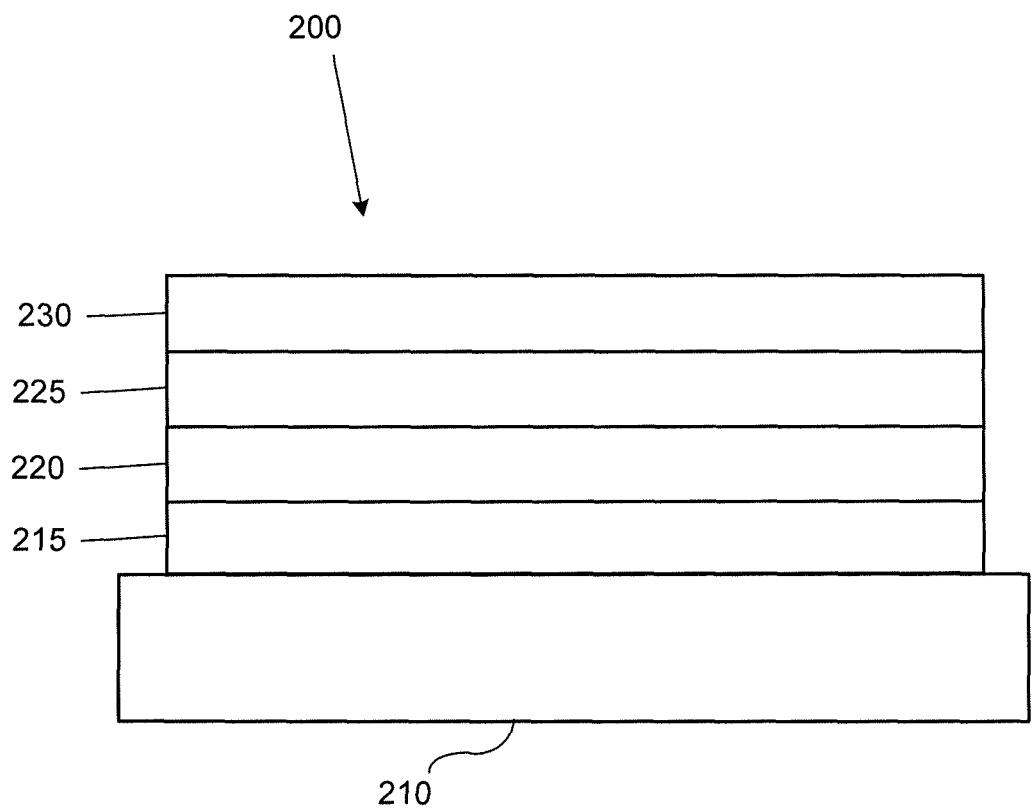
FIG. 2 shows an inverted organic light emitting device that does not have a separate electron transport layer.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al, which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve out-coupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. patent application Ser. No. 10/233,470, now U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processibility than those having symmetric structures, because asymmetric materials may have a lower tendency to recrystallize. Dendrimer substituents may be used to enhance the ability of small molecules to undergo solution processing.

Devices fabricated in accordance with embodiments of the invention may be incorporated into a wide variety of consumer products, including flat panel displays, computer monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.).

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The terms halo, halogen, alkyl, cycloalkyl, alkenyl, alkynyl, arylkyl, heterocyclic group, aryl, aromatic group, and heteroaryl are known to the art, and are defined in U.S. Pat. No. 7,279,704 at cols. 31-32, which are incorporated herein by reference.

Figure 3:
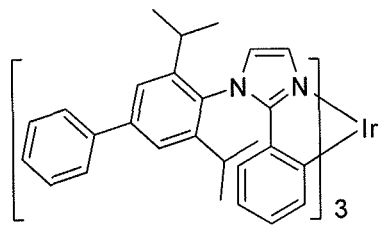
FIG. 3 shows exemplary compounds containing a twisted aryl substituent.
Figure 3:
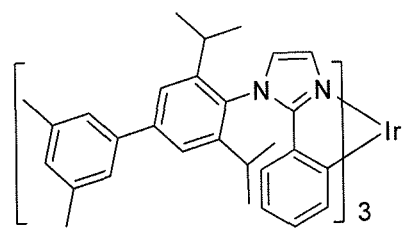
Figure 3:
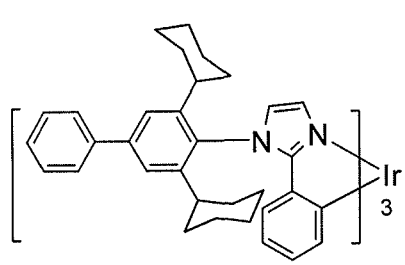
Figure 3:
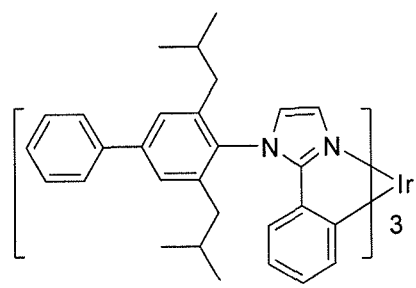
Figure 4:
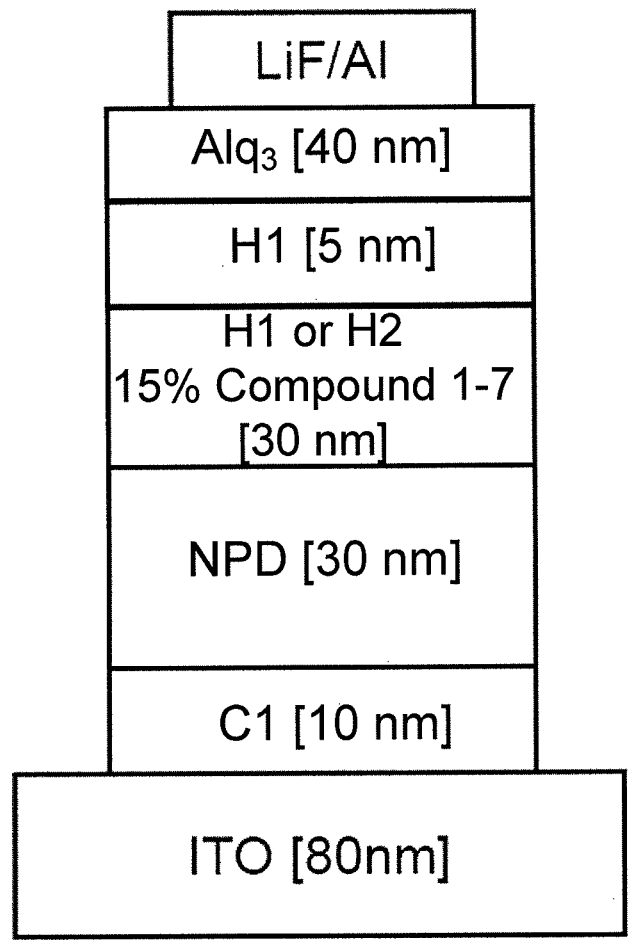
FIG. 4 shows a device structure.

Devices comprising an organic light emitting device are provided (see, FIG. 4). The organic light emitting device further comprises an organic layer containing a particular combination of materials. Specifically, the organic layer may contain 2-phenylimidazole compounds having a twisted aryl moiety with extended conjugation in combination with dibenzothiophene and dibenzofuran containing compounds. Such devices may provide improved stability, high efficiency, and reduced operating voltage. Additionally, novel 2-phenylimidazole compounds containing a twisted aryl substituent having extended conjugation are provided (see, FIG. 3).

Twisted aryl containing compounds have been reported in the literature (see, US2006/0251923 and US2007/0088167). In some cases, twisted aryls were shown to have improved stability. However, those compounds may have limited practical use. In particular, several of the previously disclosed compounds may not sublime cleanly thereby limiting their use in devices. For example, compound E3 melted and decomposed during evaporation.

The addition of an alkyl and/or aryl substituent at both ortho positions on the aryl substituent is also known. The ortho substituents may twist the aryl ring out of plane, thereby creating a twisted aryl group, which disrupts the conjugation between the imidazole and the aryl. The twisting is a result of adding a bulky group (i.e., the alkyl and/or aryl) at the ortho position of the aryl ring substituent (i.e., the C ring in Formula I). However, the steric effects created by the bulky ortho substituents may slow down the chemical reaction between the imidazole portion of the ligand and oxygen. In the earlier compounds, the LUMO is usually localized on the twisted aryl portion of the compound.

It is reported herein that compounds having increased conjugation on the twisted aryl may be surprisingly useful in organic light emitting devices when used in a particular host-dopant combination. Specifically, devices comprising compounds having increased conjugation on the twisted aryl in combination with dibenzothiophene or dibenzofuran containing compounds may result in a significant improvement in device properties. For example E1, an earlier compound, has no additional aryl substituent to increase conjugation on the twisted aryl (i.e., phenyl C ring) while inventive Compound 1 has a twisted aryl further substituted with a phenyl (i.e., a biphenyl C ring). Compound 1 demonstrated improved stability in devices and its color was only slightly shifted, as compared to E1, as a result of the additional aryl group. Therefore, compounds with twisted aryl having extended conjugation used in combination with dibenzothiophene or dibenzofuran containing compounds may provide especially good devices.

Additionally, the particular combination of twisted aryl compounds having extended conjugation and dibenzothiophene or dibenzofuran containing compounds may be especially desirable for use in blue organic light emitting devices. In particular, devices containing this particular combination of materials may provide improved lifetime and stability due to the increased stabilization of the anion or anion radical, i.e, when the material is reduced in device operation. Without being bound by theory, it is thought that a shorter excited state lifetime may result in improved device stability. Excited state lifetime measurements show that the invention compounds have a shorter excited state lifetime than previously reported twisted aryl containing compounds (see Table 4). Therefore, the combination of twisted aryl compounds having extended conjugation with dibenzothiophene or dibenzofuran containing materials may be particularly useful in blue devices.

A first device comprising an organic light emitting device is provided. The organic light emitting device further comprises an anode, a cathode, and an organic layer, disposed between the anode and the cathode, the organic layer comprising a first compound itself comprising a ligand having the structure:

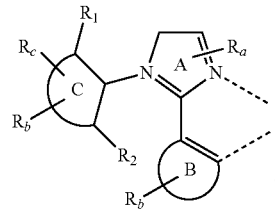

Formula I

B and C are each independently a 5 or 6-membered carbocyclic or heterocyclic ring. A-B and A-C each represent a bonded pair of carbocyclic or heterocyclic rings. $R_a$, $R_b$, and $R_c$ may represent mono, di, tri, or tetra substitutions. $R_a$, $R_b$, and $R_c$ are independently selected from the group consisting of hydrogen, halogen, alkyl, alkoxy, amino, alkenyl, alkynyl, arylalkyl, aryl and heteroaryl. $R_1$ and $R_2$ are ortho substituents on ring C (i.e., $R_1$ and $R_2$ are positioned ortho to the carbon atom of ring C that is bonded to the nitrogen atom of ring A). $R_1$ and $R_2$ are independently selected from the group consisting of hydrogen, alkyl, alkoxy, amino, alkenyl, alkynyl, arylalkyl, aryl and heteroaryl. Ar is a 5 or 6-membered carbocyclic or heterocyclic ring. The ligand L is coordinated to a metal M having an atomic number greater than 40. Preferably, the metal M is Ir.

Moreover, the organic layer comprises a second compound having the formula:

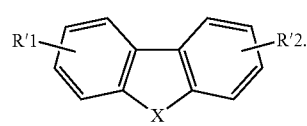

Formula II

X is S or O. Preferably, X is S. $R'_1$ and $R'_2$ are independently selected from the group consisting of hydrogen, alkyl, alkoxy, amino, alkenyl, alkynyl, arylalkyl, aryl and heteroaryl. In one aspect, one of $R'_1$ and $R'_2$ is carbazole. In another aspect, $R'_1$ and $R'_2$ are carbazole.

Preferably, at least one of $R_1$ and $R_2$ is an alkyl. More preferably, at least one of $R_1$ and $R_2$ is an alkyl having 2 or more carbon atoms. Preferably, each of $R_1$ and $R_2$ is an alkyl. More preferably, each of $R_1$ and $R_2$ is an alkyl having 2 or more carbon atoms.

In one aspect, B is benzene. Devices comprising an OLED which itself contains phenylimidazole compounds comprising a twisted aryl with extended conjugation (i.e., compounds having Formula I wherein B is benzene) may be especially beneficial. For example, devices with a phenylimidazole containing compound may have improved stability and efficiency.

As used herein, Ar refers to a mandatory substitution on the C ring. Ar is defined herein as a 5 or 6-membered carbocyclic or heterocyclic ring. The Ar substituent provides the extended conjugation of the twisted aryl moiety of the compounds (i.e., C ring). In Formula I, Ar is a required substituent of the C ring but the position of the Ar substituent is not specified. In other words, Ar may be located meta or para to the carbon atom in the C ring that is bonded to the nitrogen atom in the imidazole A ring (i.e., in any position within the C ring other than the positions $R_1$ and $R_2$). Preferably, Ar is para to the carbon atom which is bonded to the nitrogen atom in the A ring.

In one aspect, devices are provided wherein the compound has the formula:

Formula III

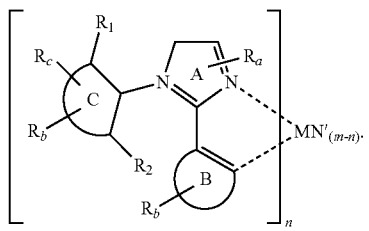

m is the oxidation state of the metal M. n is at least 1. L' is a monoanionic bidentate ligand. L' may be selected from the group consisting of:

FORMULA IV

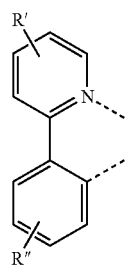

FORMULA V

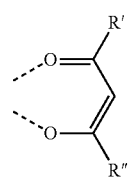

FORMULA VI

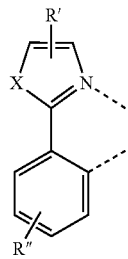

FORMULA VII

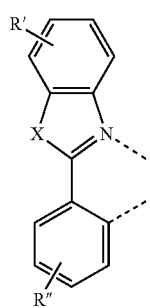

-continued

FORMULA VIII

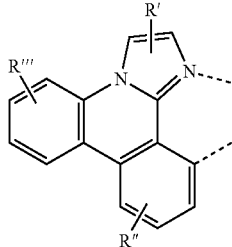

FORMULA IX

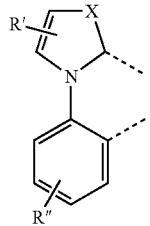

FORMULA X

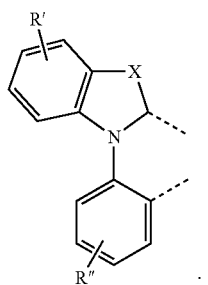

R', R", and R''' are independently selected from the group consisting of hydrogen, halogen, alkyl, alkoxy, amino, alkenyl, alkynyl, arylalkyl, aryl, and heteroaryl. X is selected from the group consisting of S, NZ, O, Se, BZ, CZZ', and C=O. Z and Z' are independently selected from the group consisting of hydrogen, alkyl, and aryl.

Particular devices are provided, wherein the device contains a first compound selected from the group consisting of:

Compound 1

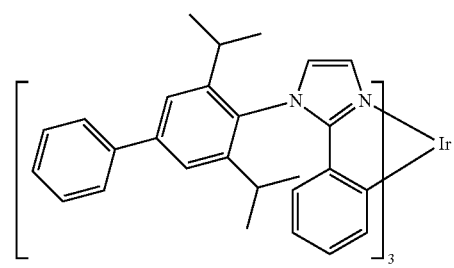

Compound 2

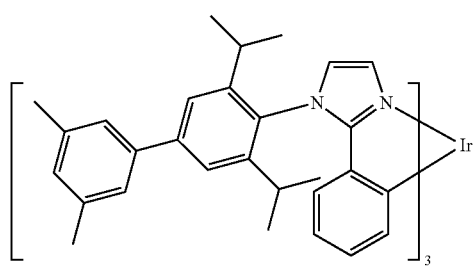

Compound 3
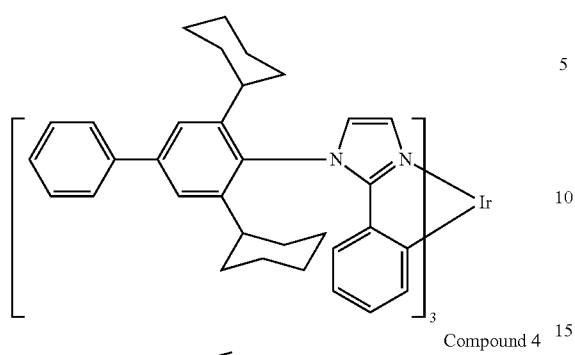
Compound 4
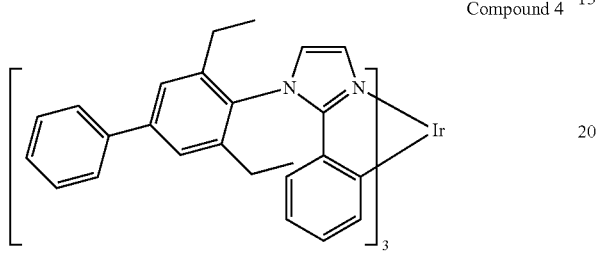
Compound 5
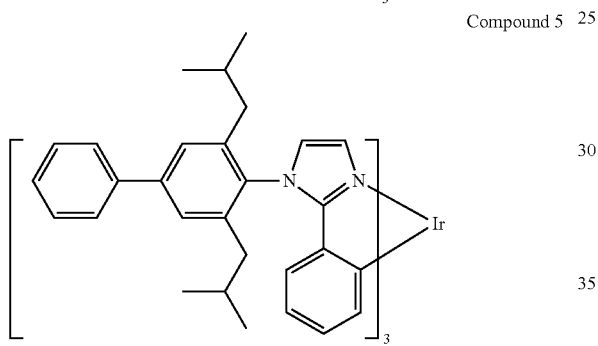
Compound 6
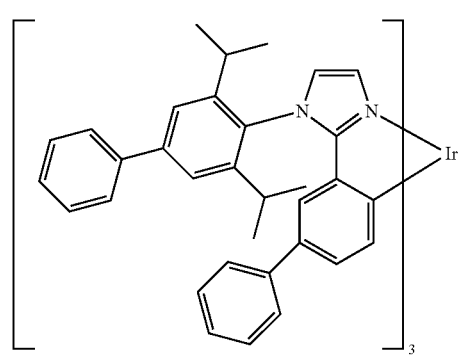
Compound 7
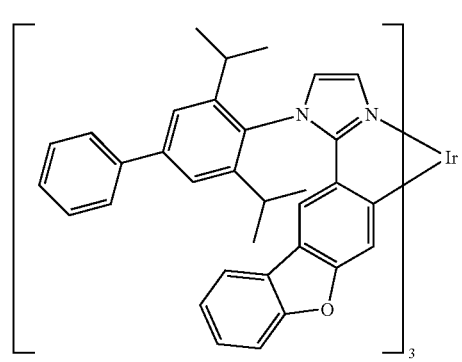
Compound 8
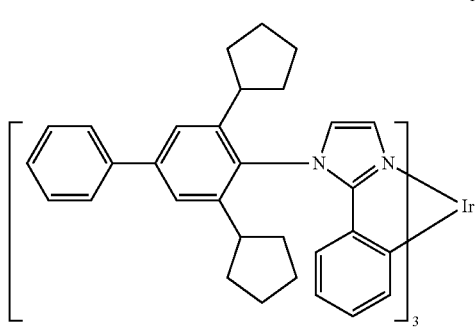
Compound 9
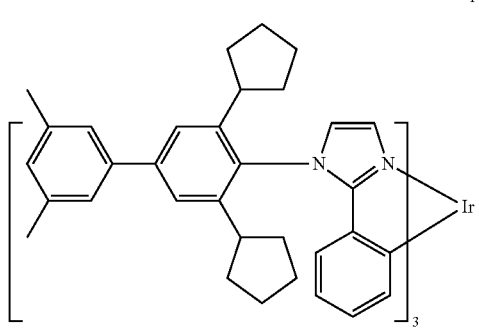
Compound 10
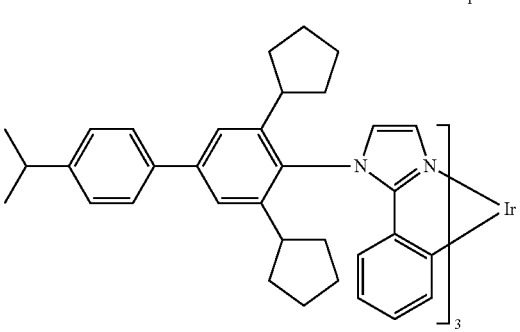
Compound 11
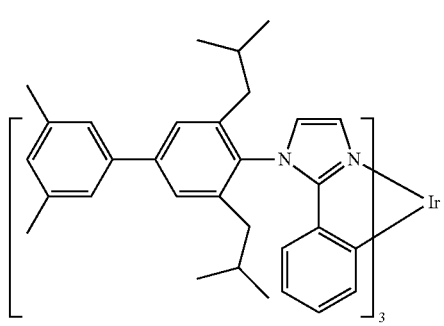

Compound 12
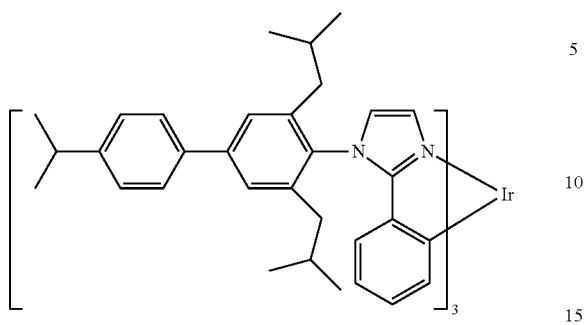
Compound 13
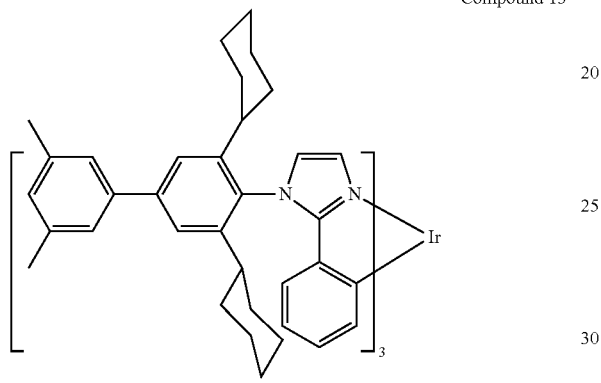
Compound 14
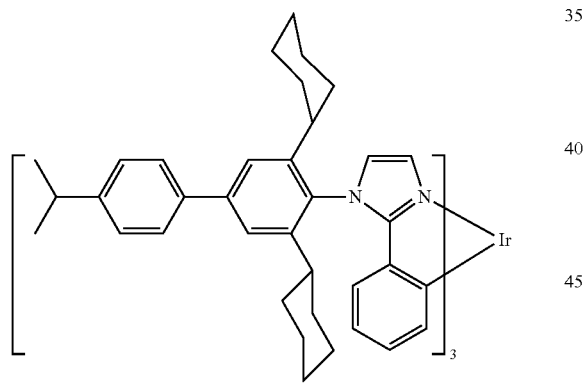
Compound 15
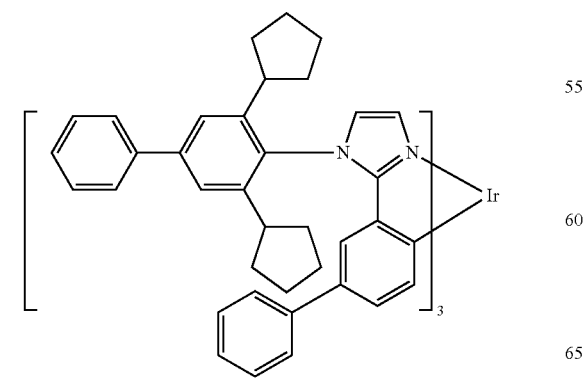
Compound 16
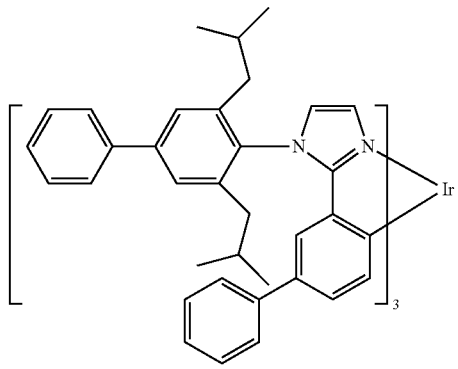
Compound 17
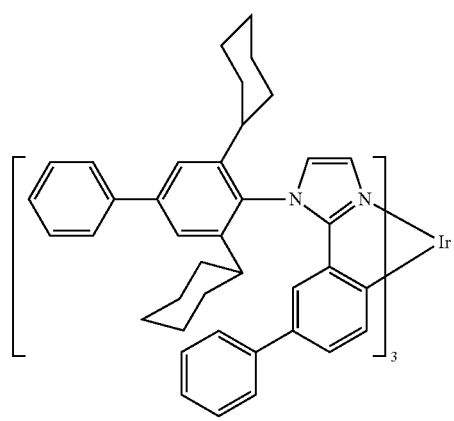
Compound 18
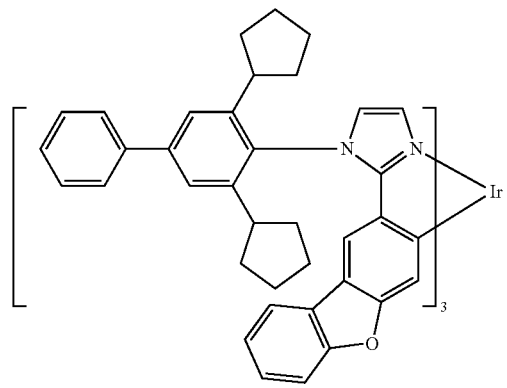
Compound 19
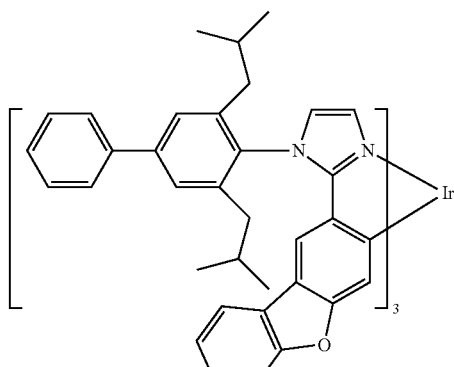

Compound 20
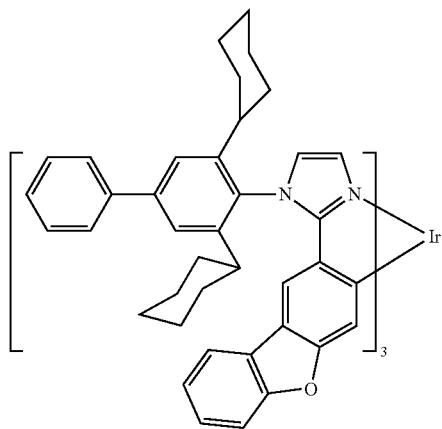
Compound 21
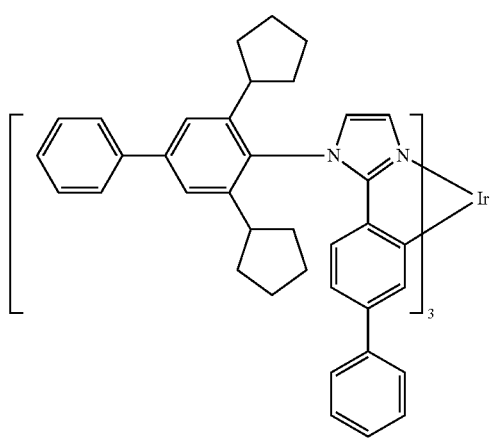
Compound 22
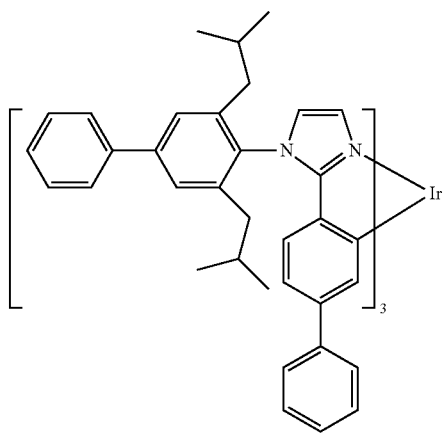
Compound 23
Compound 24
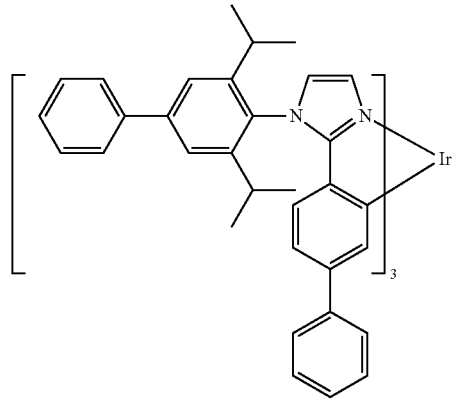
Compound 25
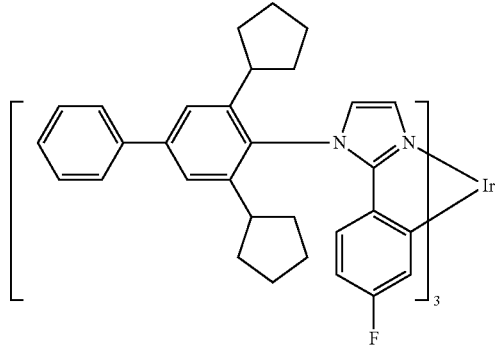

Compound 26
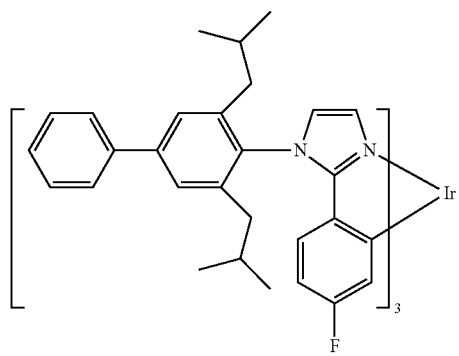
Compound 27
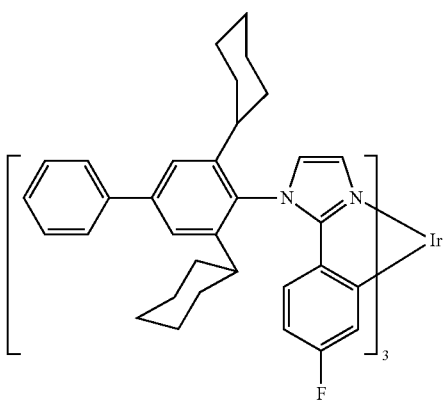
Compound 28
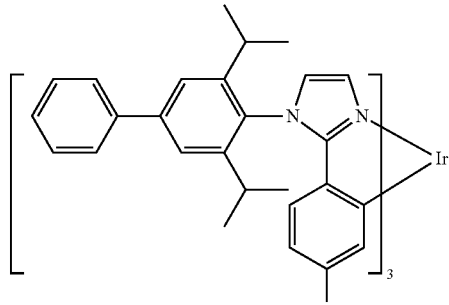
Compound 29
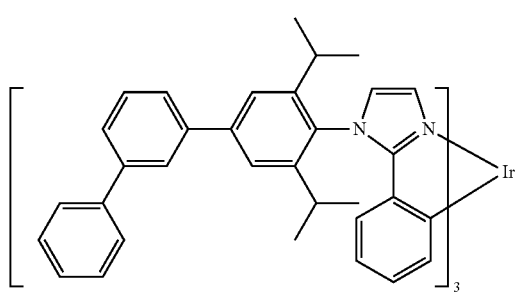
Compound 30
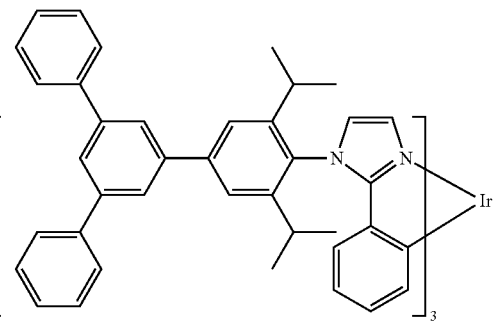
Compound 31
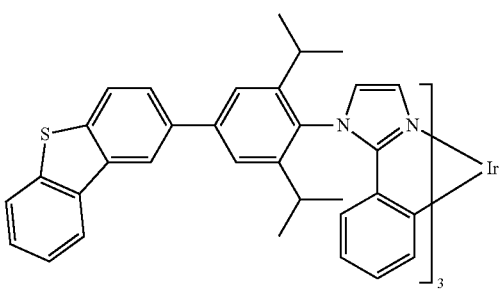
Compound 32
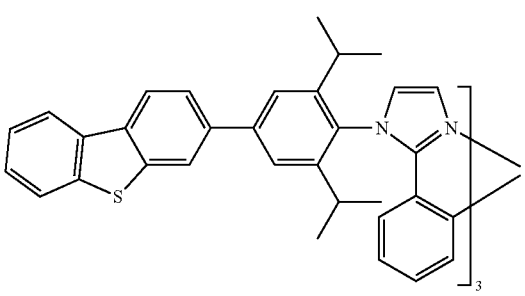
Compound 33
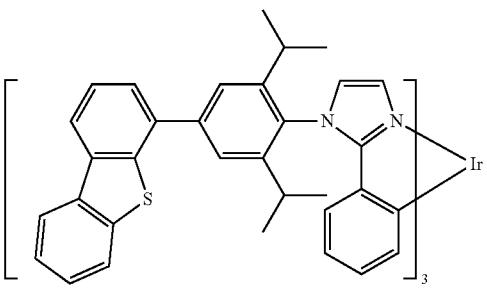
Compound 34
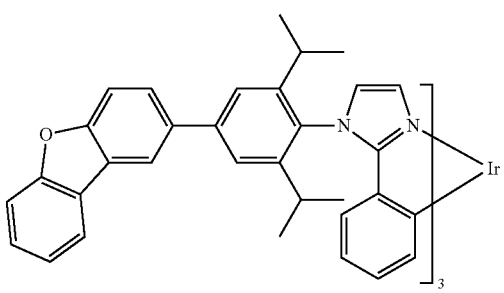

Compound 35
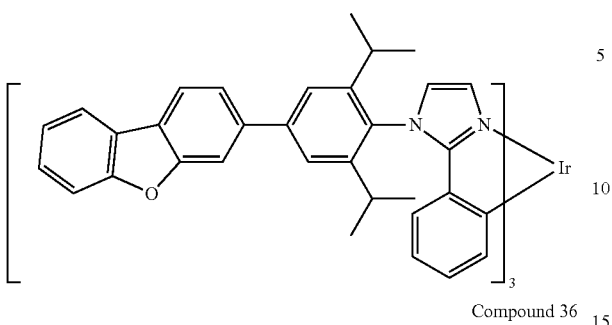
Compound 36
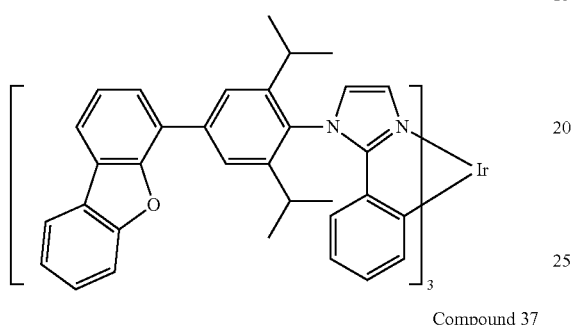
Compound 37
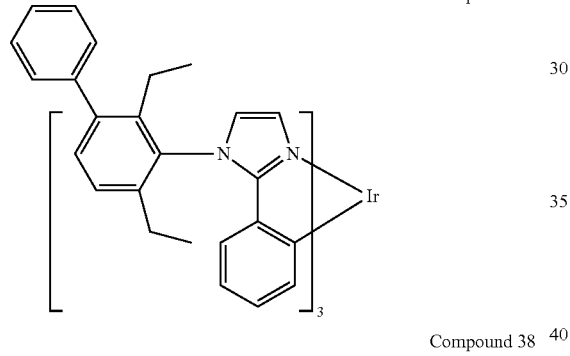
Compound 38
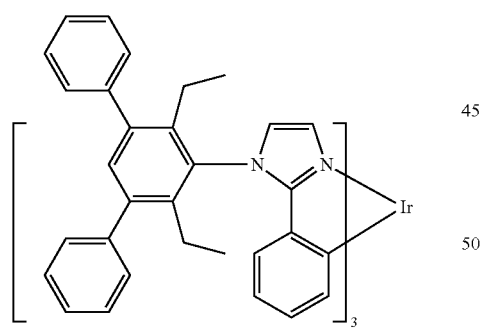
Compound 39
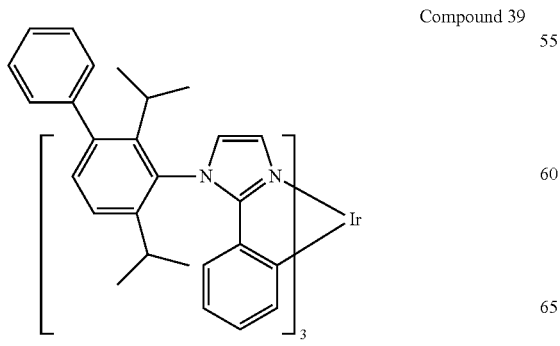
Compound 40
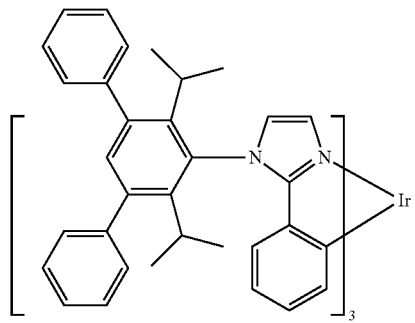
Compound 41
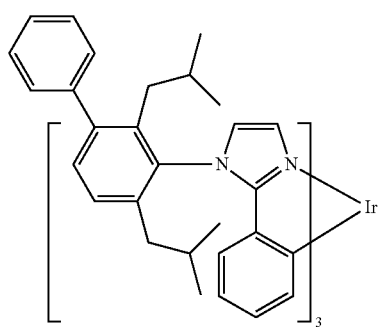
Compound 42
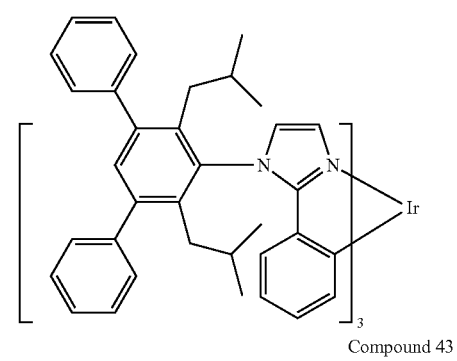
Compound 43
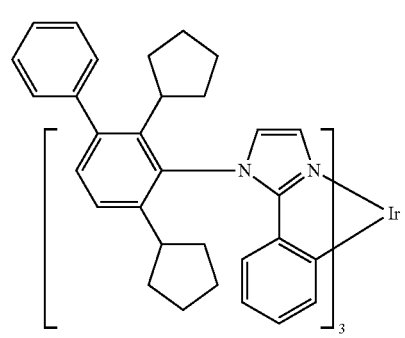
Compound 44
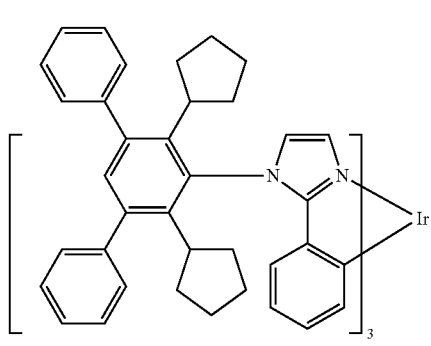

Compound 45
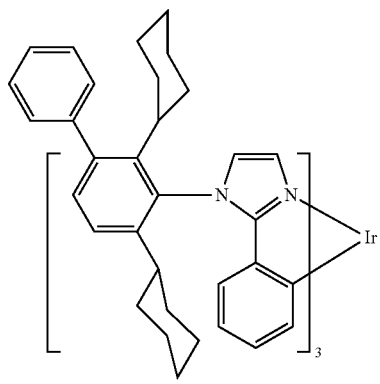
Compound 46
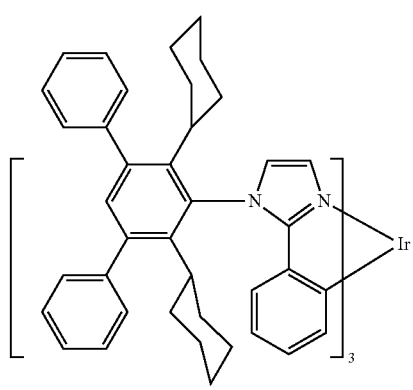
Compound 47
Compound 48
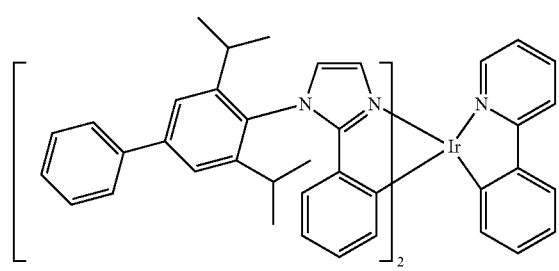
Compound 49
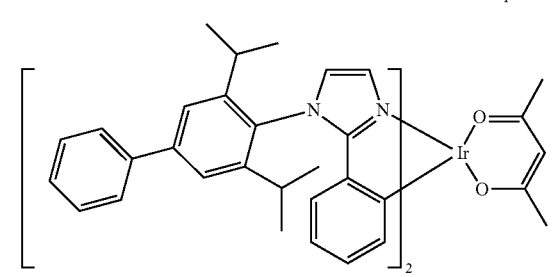
Compound 50
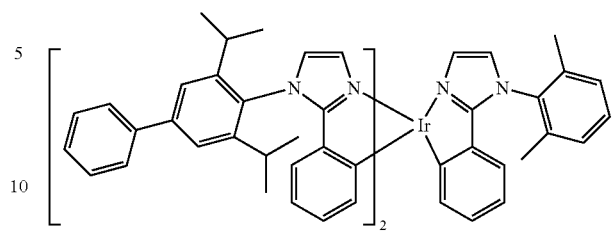
Compound 51
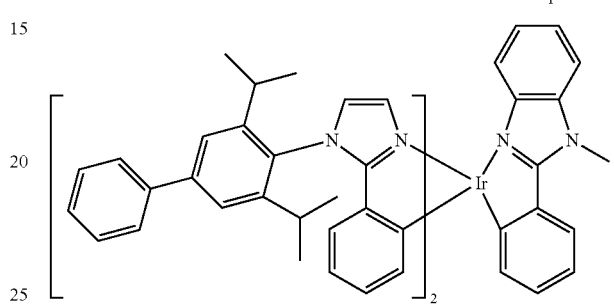
Compound 52
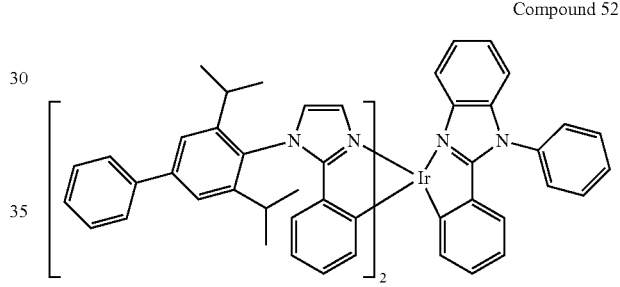
Compound 53
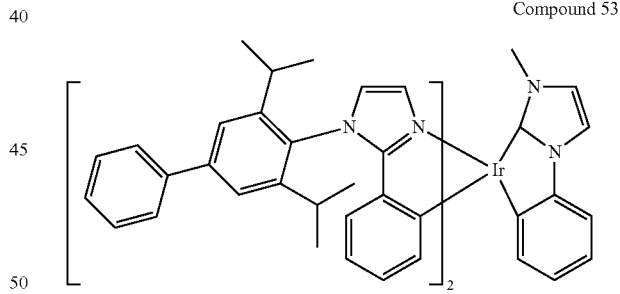
Compound 54
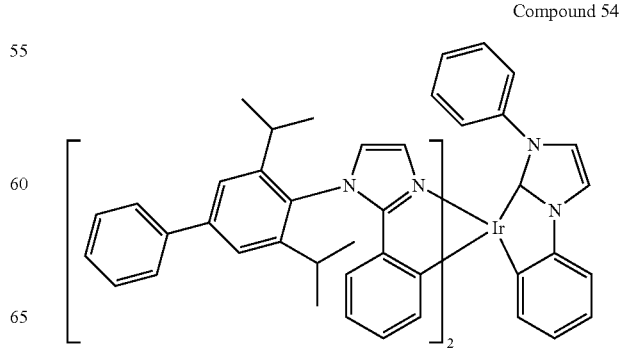

Compound 55
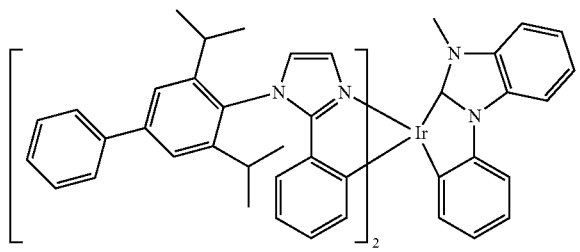
Compound 56
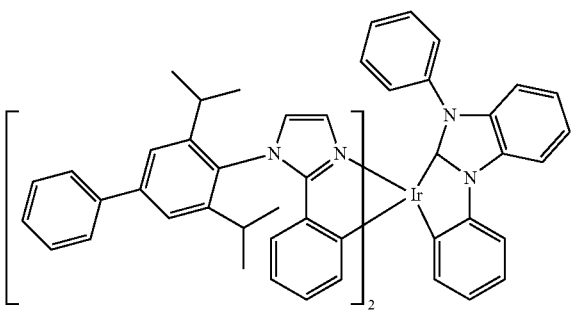
Compound 57
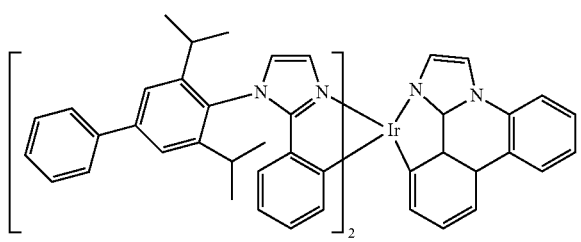
Compound 58
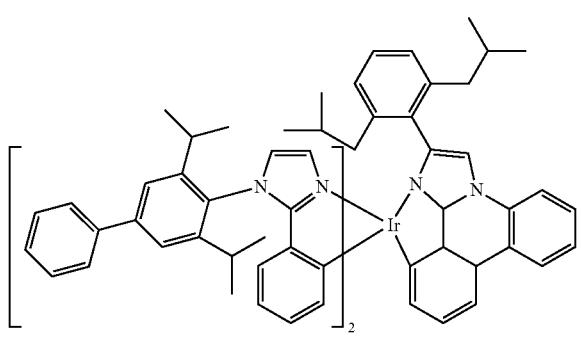
Compound 59
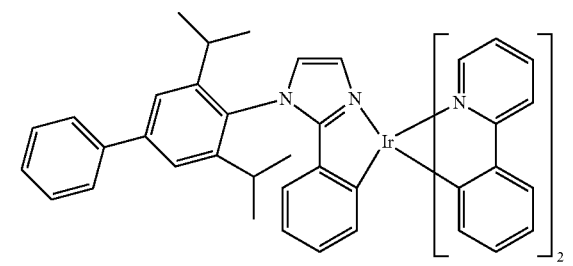
Compound 60
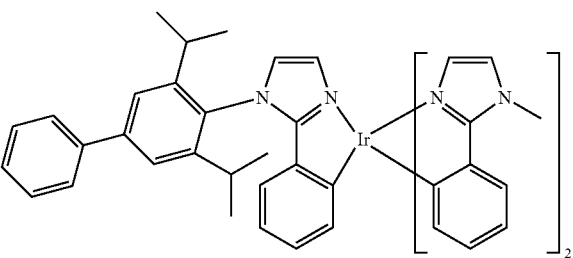
Compound 61
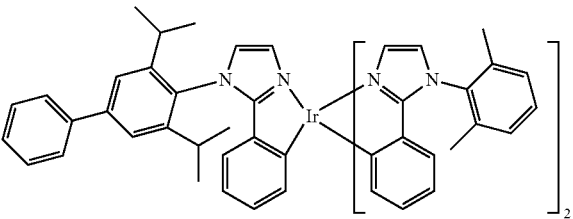
Compound 62
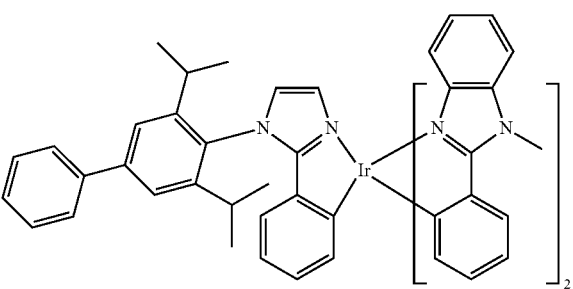
Compound 63
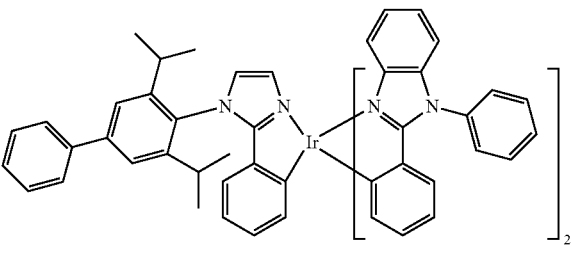
Compound 64
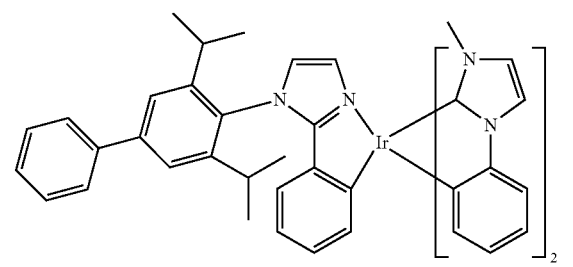

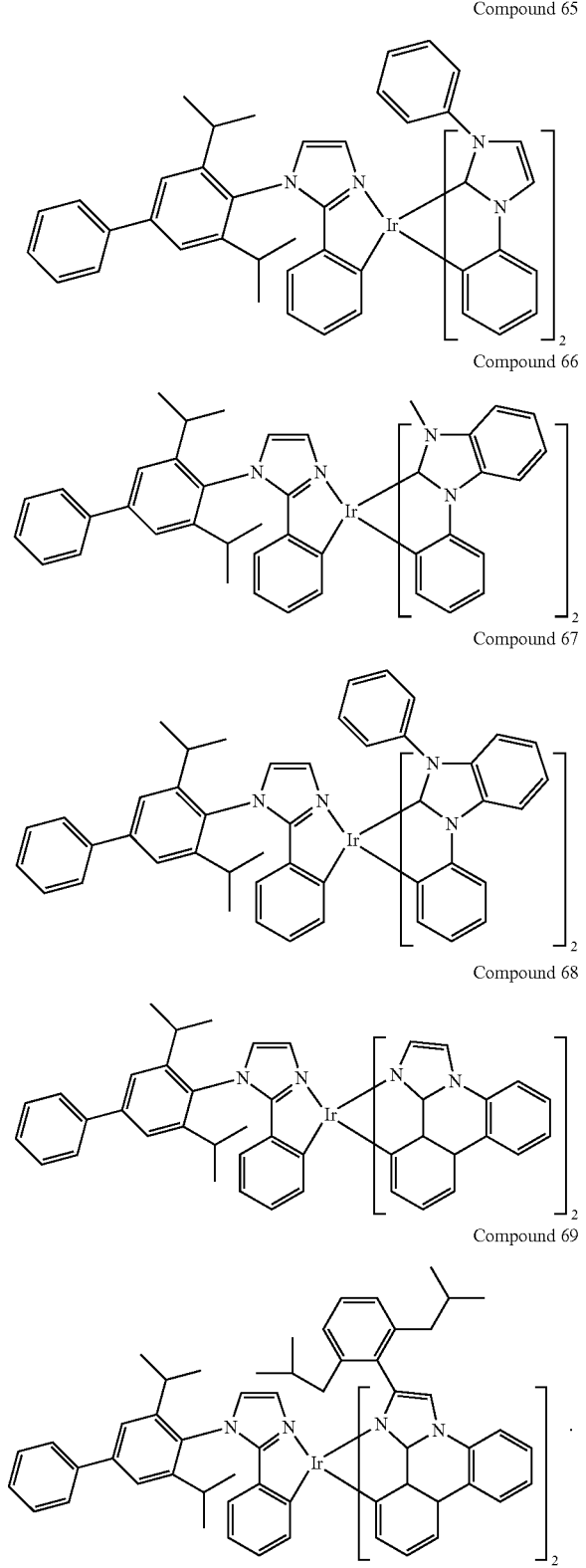

Compound 65

Compound 66

Compound 67

Compound 68

Compound 69

The devices may contain homoleptic compounds or heteroleptic compounds. Non-limiting examples of homoleptic compounds include Compound 1-Compound 46. Non-limiting examples of heteroleptic compounds include Compound 47-Compound 69.

Preferably, the first compound selected from the group consisting of Compound 1, Compound 2, Compound 3, and Compound 5. More preferably, the first compound is Compound 1.

In one aspect, the organic layer is an emissive layer and the first compound is an emitting dopant and the second compound is a host.

Devices containing particular compounds, specifically certain emitting dopants and certain host materials in combination, may be especially desirable. In one aspect, the device may comprise at least one of Compounds 1-69 and a compound having Formula II wherein at least one of Compounds 1-69 is the emitting dopant and a compound having Formula II is the host. In another aspect, the device may comprise H1 and at least one of Compound 1, 2, 3, and 5 wherein H1 is the host and at least one of Compound 1, 2, 3, and 5 is the emitting dopant. Preferably, the device contains Compound 1 as the emitting dopant in combination with H1 as the host material. In another aspect, the device may comprise H2 as the host material and Compound 1 as the emitting dopant. These devices may have especially beneficial properties, such as improved manufacturing and longer lifetime.

Additionally, specific compounds are provided. The compounds contain a phenylimidazole ligand having a twisted aryl moiety. The twisted aryl itself has both ortho positions substituted and has extended conjugation. The compound is selected from the group consisting of:

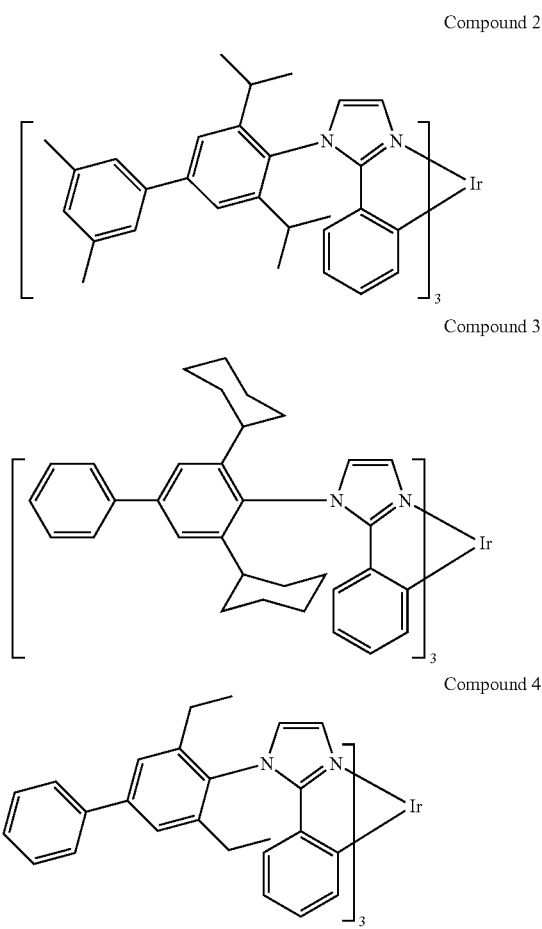

Compound 2

Compound 3

Compound 4

Compound 5
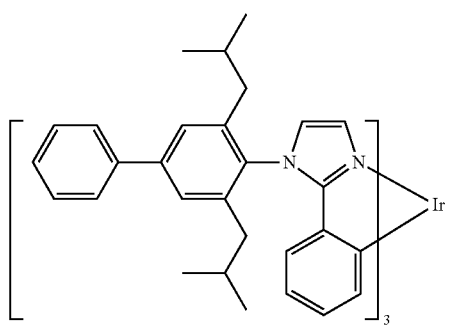
Compound 6
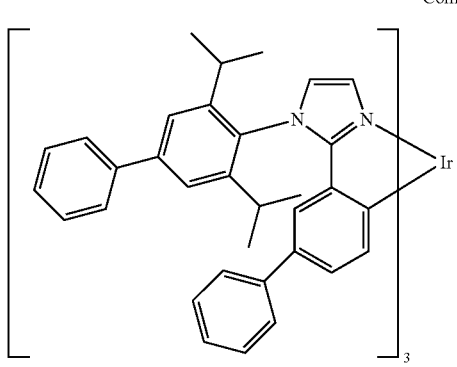
Compound 7
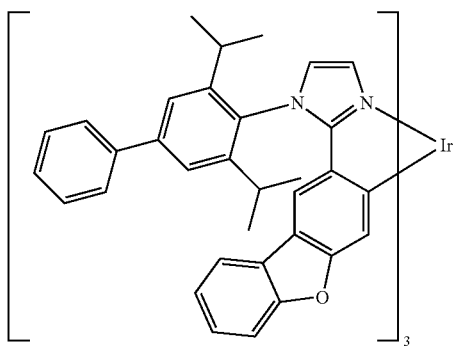
Compound 8
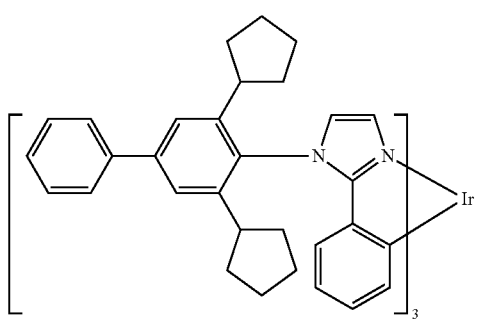
Compound 9
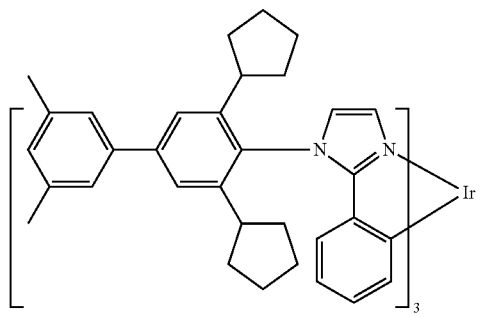
Compound 10
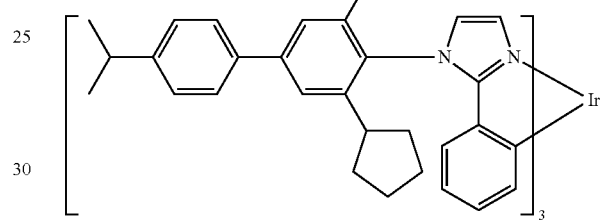
Compound 11
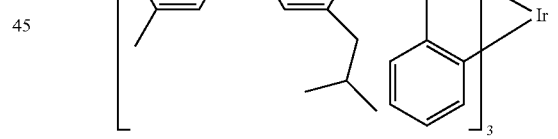
Compound 12
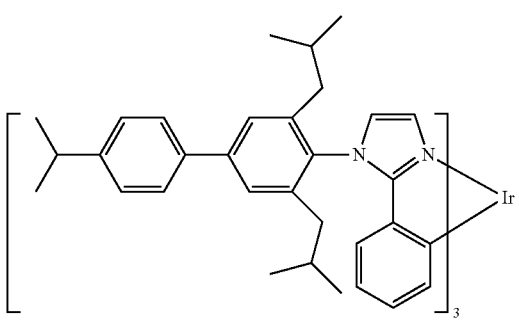

Compound 13
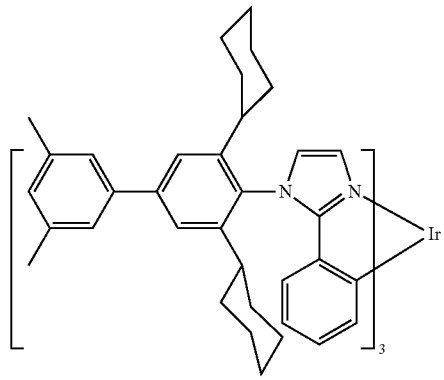
Compound 14
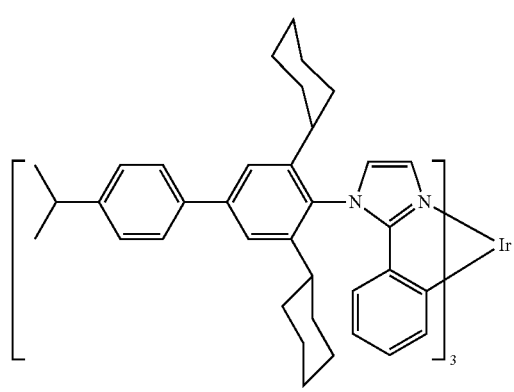
Compound 15
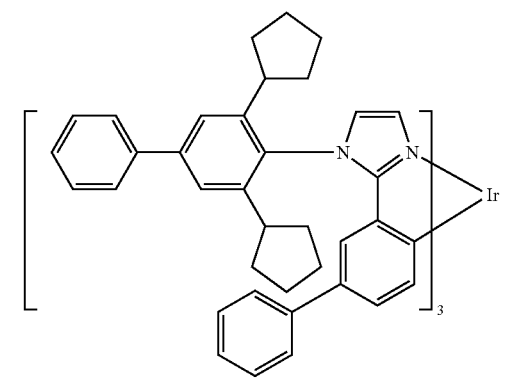
Compound 16
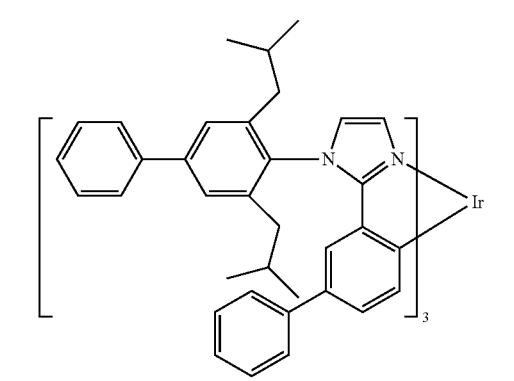
Compound 17
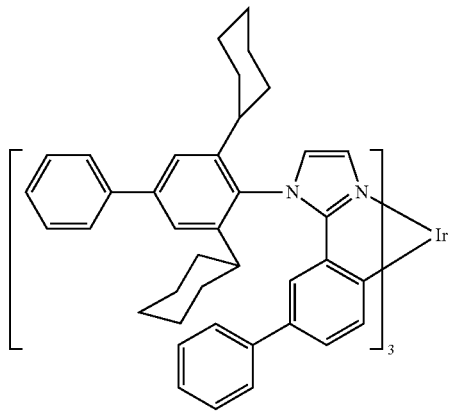
Compound 18
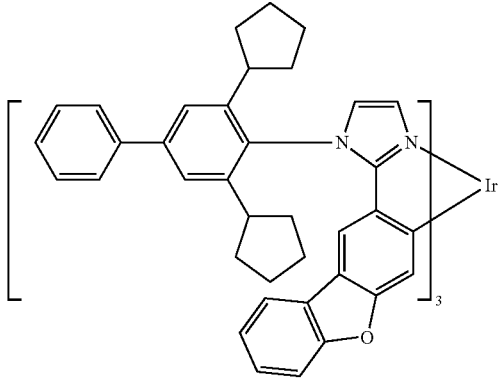
Compound 19
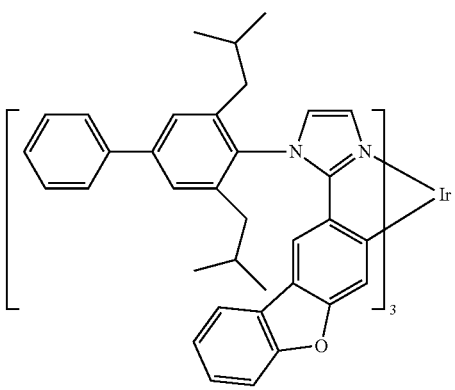

Compound 20
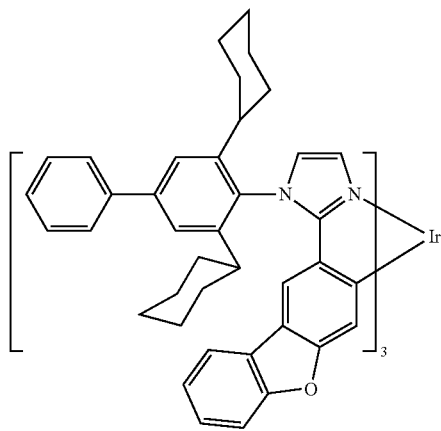
Compound 21
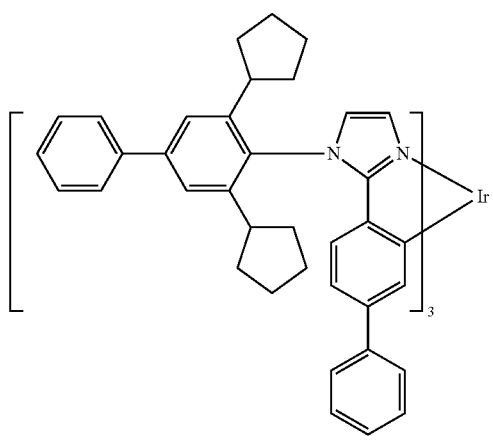
Compound 22
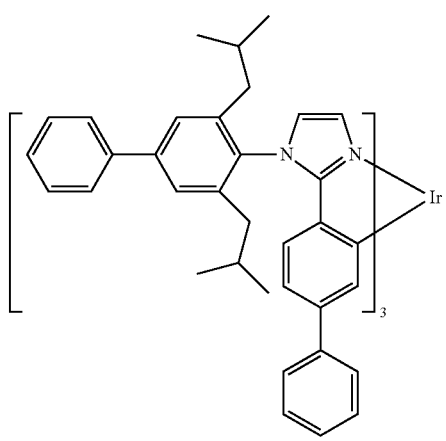
Compound 23
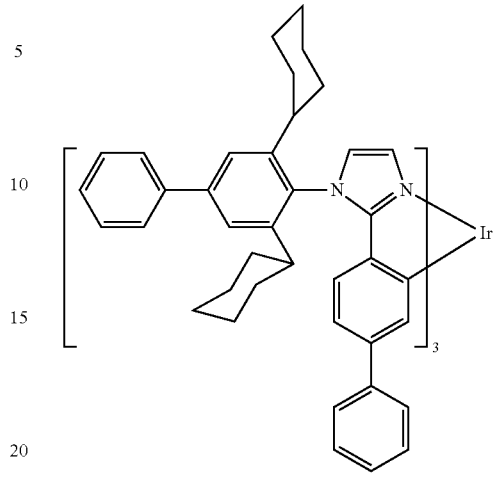
Compound 24
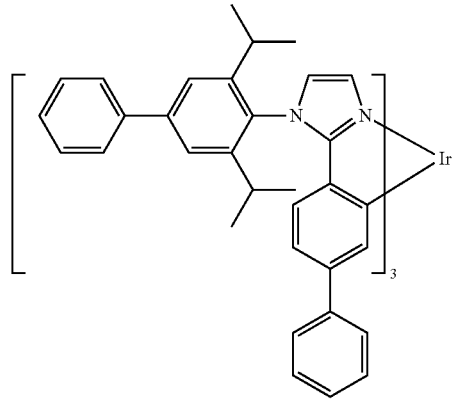
Compound 25
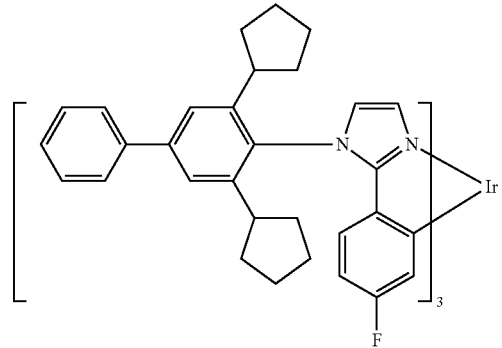

Compound 26
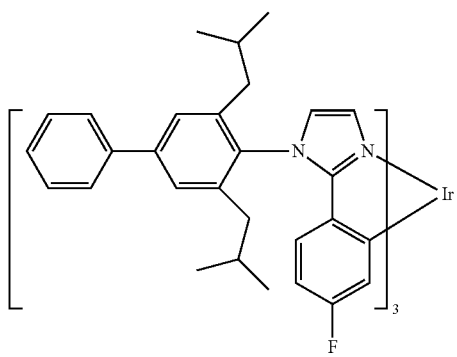
Compound 27
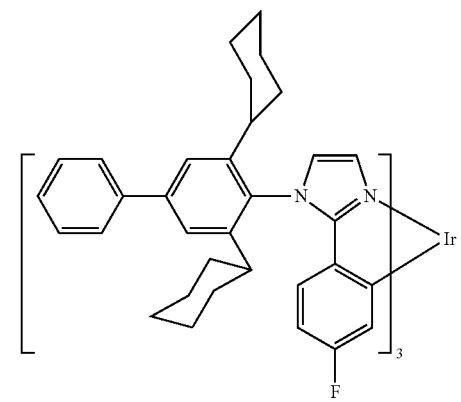
Compound 28
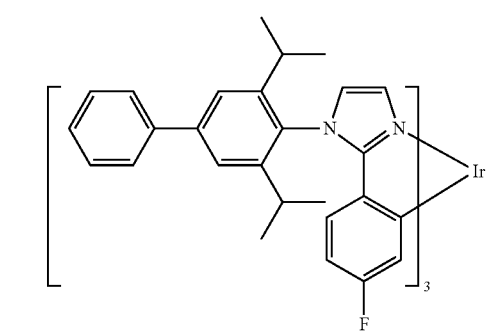
Compound 29
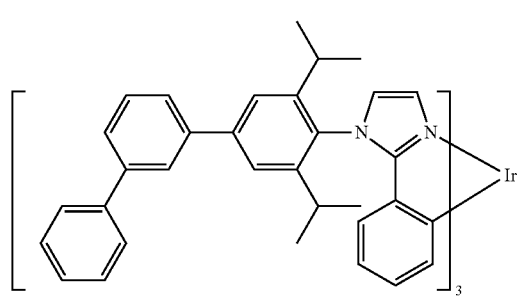
Compound 30
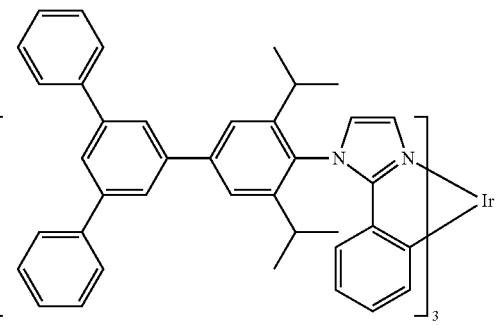
Compound 31
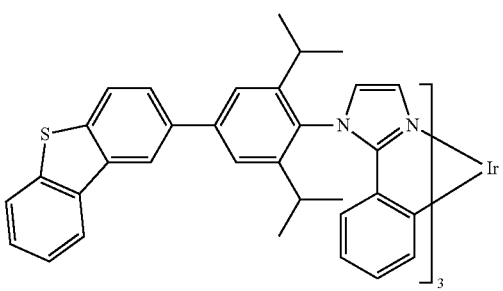
Compound 32
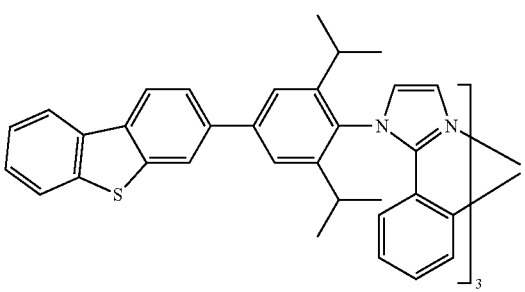
Compound 33
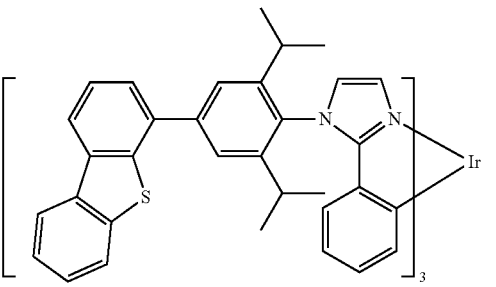
Compound 34
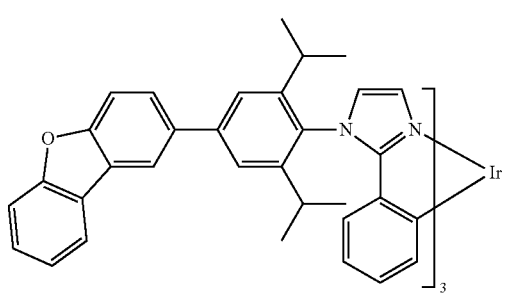

Compound 35
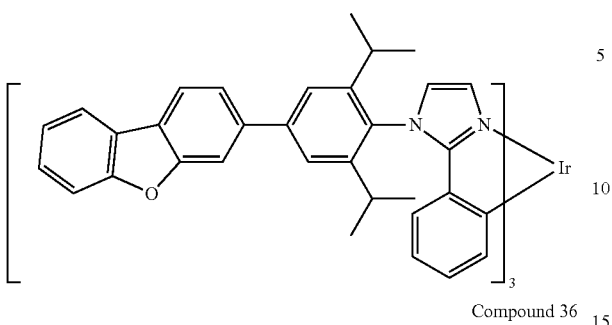
Compound 36
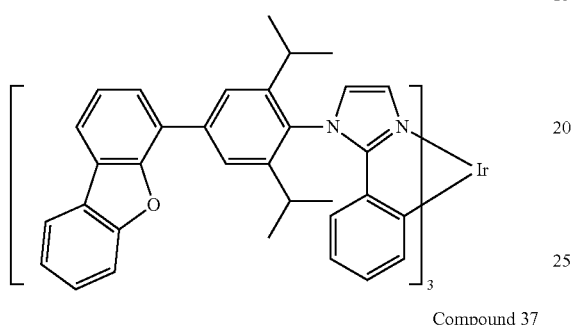
Compound 37
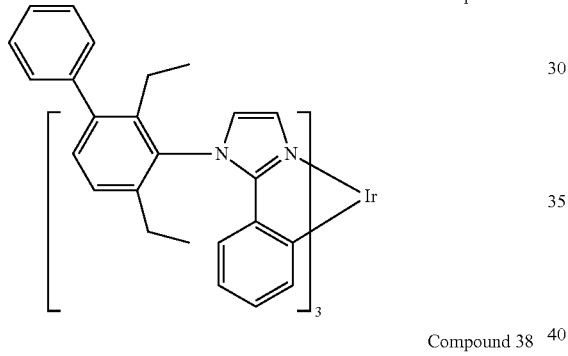
Compound 38
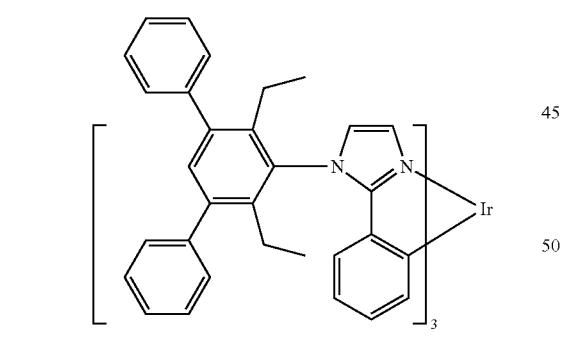
Compound 39
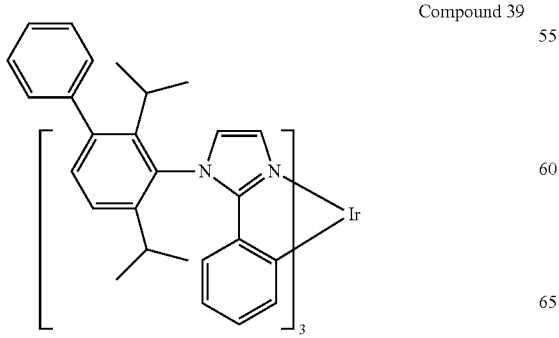
Compound 40
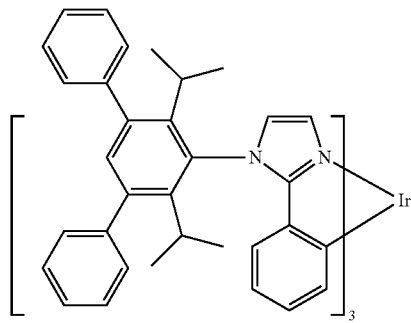
Compound 41
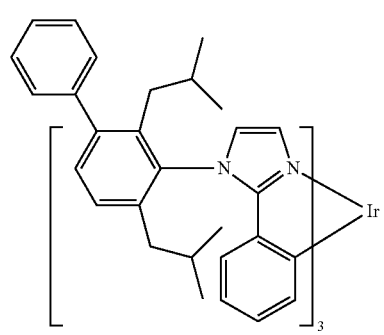
Compound 42
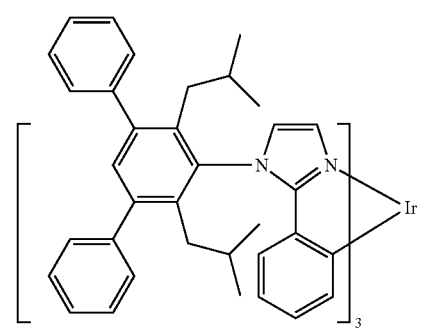
Compound 43
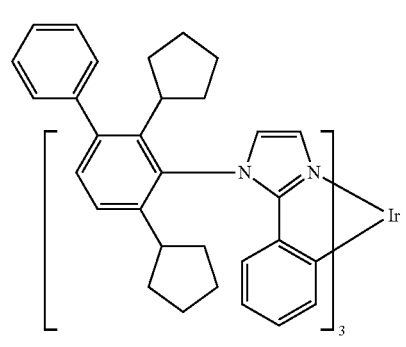
Compound 44
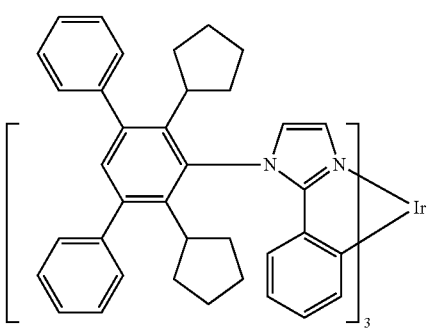

Compound 45
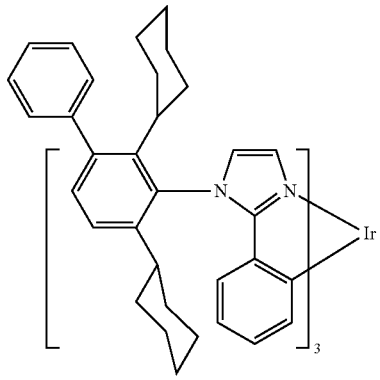
Compound 46
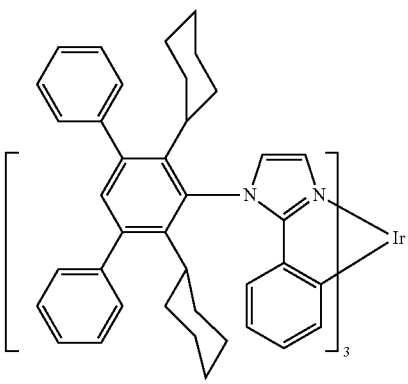
Compound 47
Compound 48
Compound 49
Compound 50
Compound 51
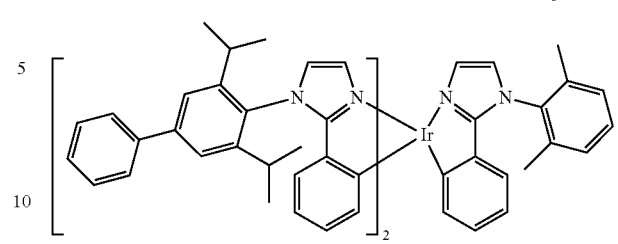
Compound 52
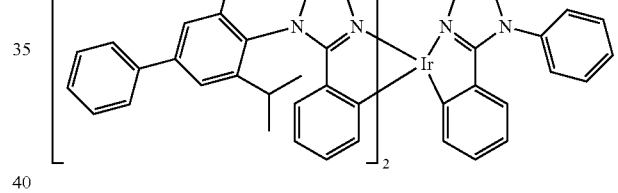
Compound 53
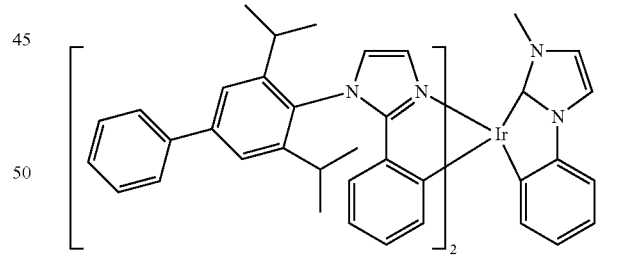
Compound 54
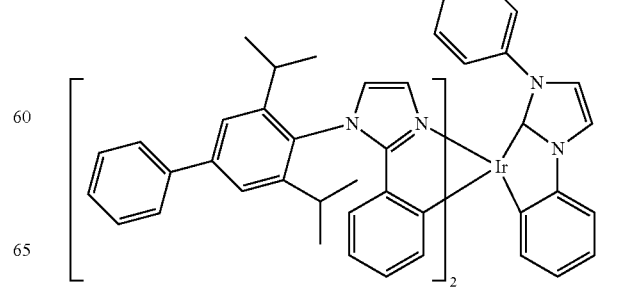

Compound 55
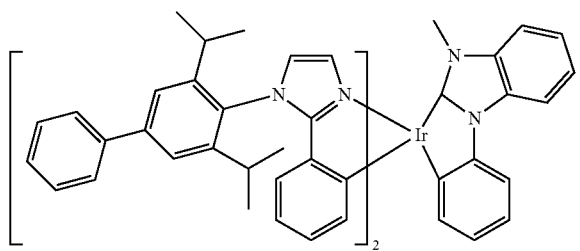
Compound 60
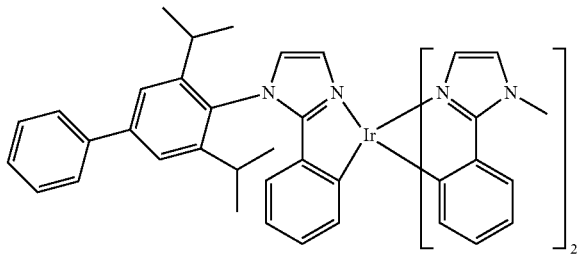
Compound 56
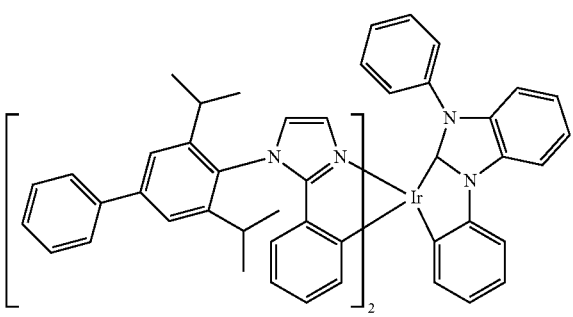
Compound 61
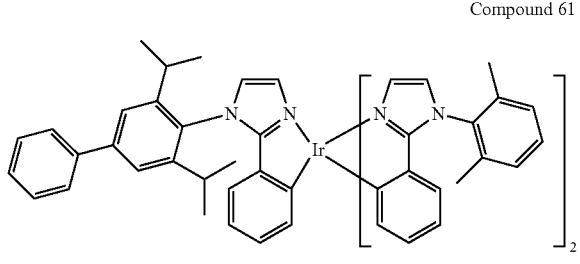
Compound 57
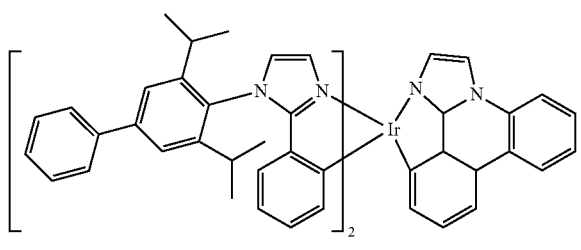
Compound 62
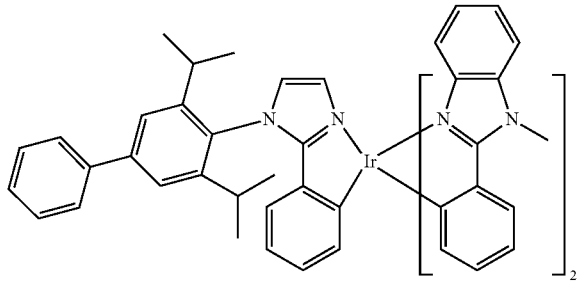
Compound 58
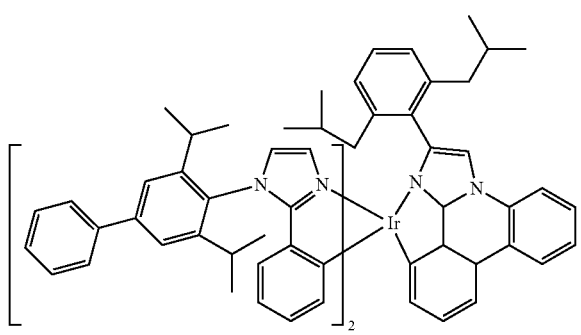
Compound 63
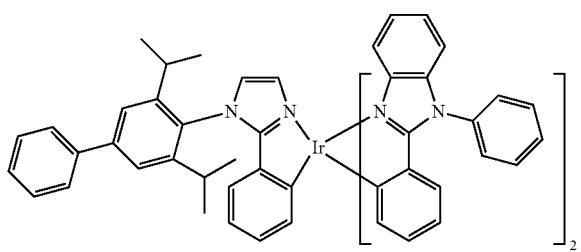
Compound 59
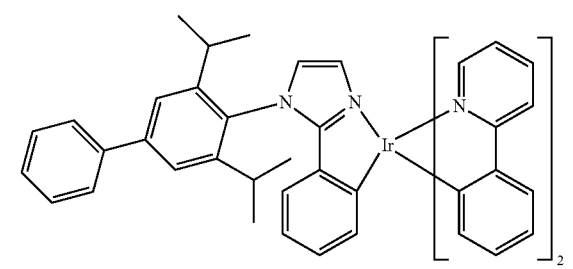
Compound 64
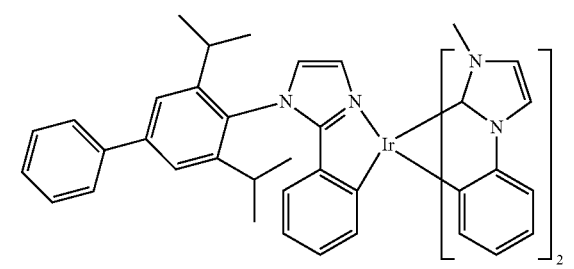

Compound 65

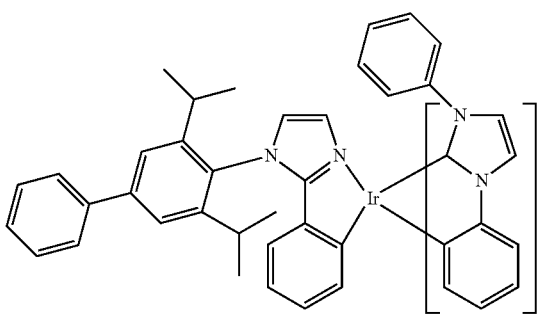

Compound 66

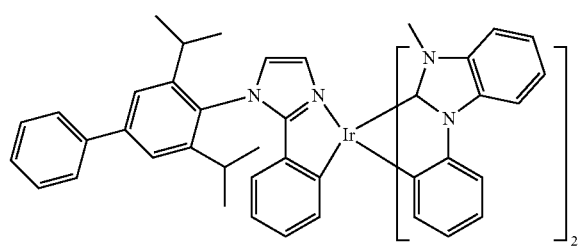

Compound 67

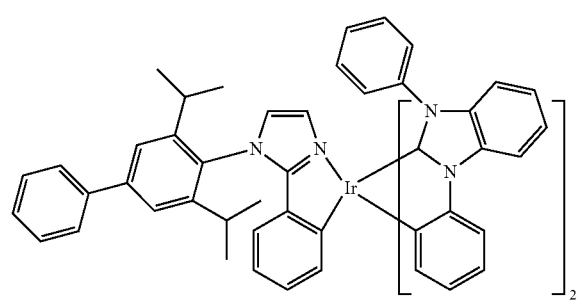

Compound 68

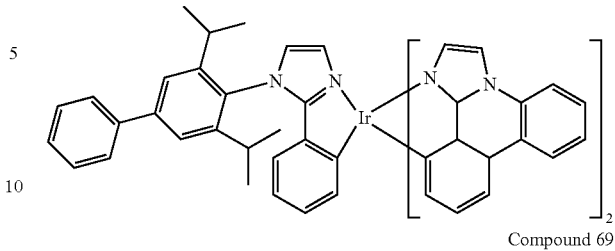

Compound 69

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

In addition to and/or in combination with the materials disclosed herein, many hole injection materials, hole transporting materials, host materials, dopant materials, exiton/hole blocking layer materials, electron transporting and electron injecting materials may be used in an OLED. Non-limiting examples of the materials that may be used in an OLED in combination with materials disclosed herein are listed in Table 1 below. Table 1 lists non-limiting classes of materials, non-limiting examples of compounds for each class, and references that disclose the materials.

TABLE 1

| MATERIAL | EXAMPLES OF MATERIAL | PUBLICATIONS |
|---|---|---|
| Hole injection materials | | |
| Phthalocyanine and porphryin compounds | | Appl. Phys. Lett. 69, 2160 (1996) |

TABLE 1-continued

| MATERIAL | EXAMPLES OF MATERIAL | PUBLICATIONS |
|---|---|---|
| Starburst triarylamines | 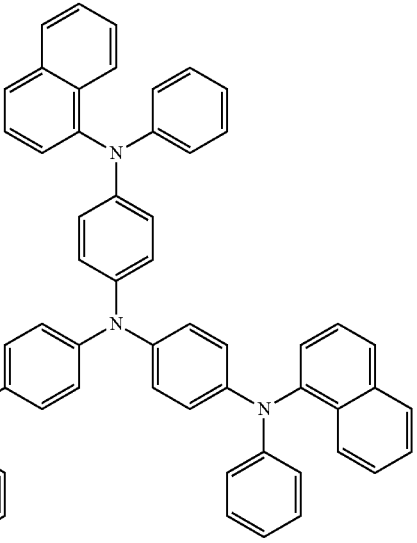 | J. Lumin. 72-74, 985 (1997) |
| $CF_x$ Fluorohydrocarbon polymer | 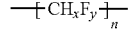 | Appl. Phys. Lett. 78, 673 (2001) |
| Conducting polymers (e.g., PEDOT:PSS, polyaniline, polypthiophene) | 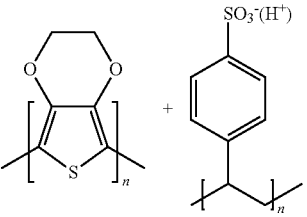 | Synth. Met. 87, 171 (1997) |
| Arylamines complexed with metal oxides such as molybdenum and tungsten oxides | 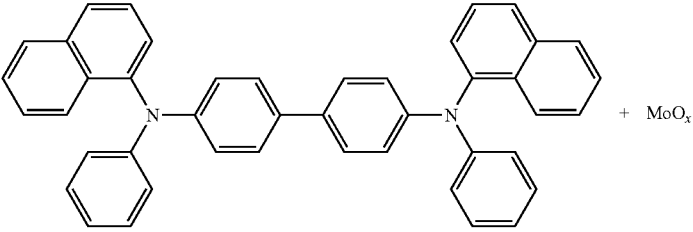 [SMILES: c1ccc(N(c2ccc(-c3ccc(N(c4ccccc4)c4cccc5ccccc45)cc3)cc2)c2cccc3ccccc23)cc1] | SID Symposium Digest, 37, 923 (2006) |
| Hole transporting materials | | |
| Triarylamines (e.g., TPD, α-NPD) | 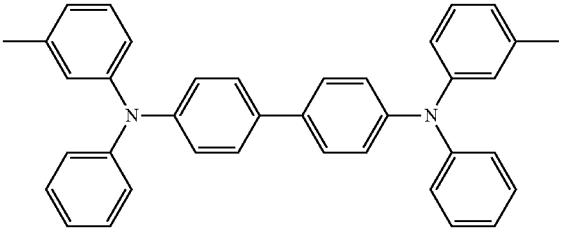 | Appl. Phys. Lett. 51, 913 (1987) |
| | 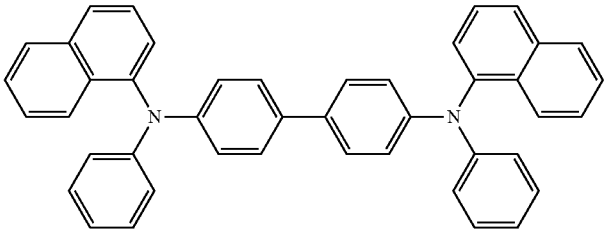 [SMILES: c1ccc(N(c2ccc(-c3ccc(N(c4ccccc4)c4cccc5ccccc45)cc3)cc2)c2cccc3ccccc23)cc1] | US5061569 |

US 8,586,204 B2
47 48
TABLE 1-continued
| MATERIAL | EXAMPLES OF MATERIAL | PUBLICATIONS |
|---|---|---|
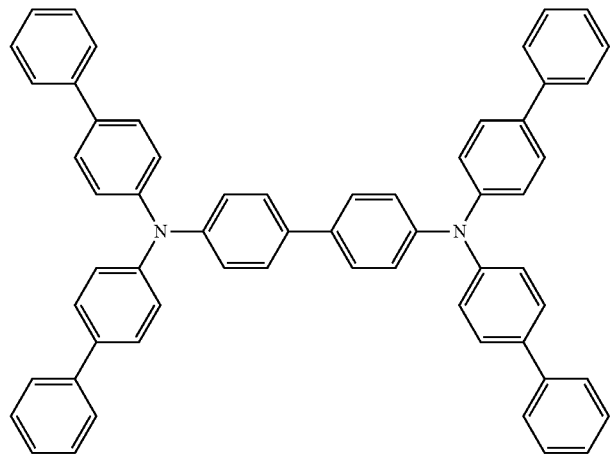 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1]
EP650955
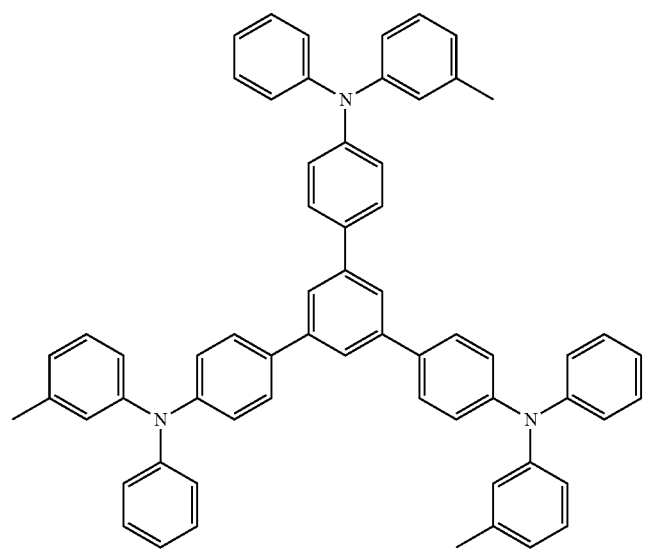 [SMILES: Cc1cccc(N(c2ccccc2)c2ccc(-c3cc(-c4ccc(N(c5ccccc5)c5cccc(C)c5)cc4)cc(-c4ccc(N(c5ccccc5)c5cccc(C)c5)cc4)c3)cc2)c1]
J. Mater. Chem. 3, 319 (1993)
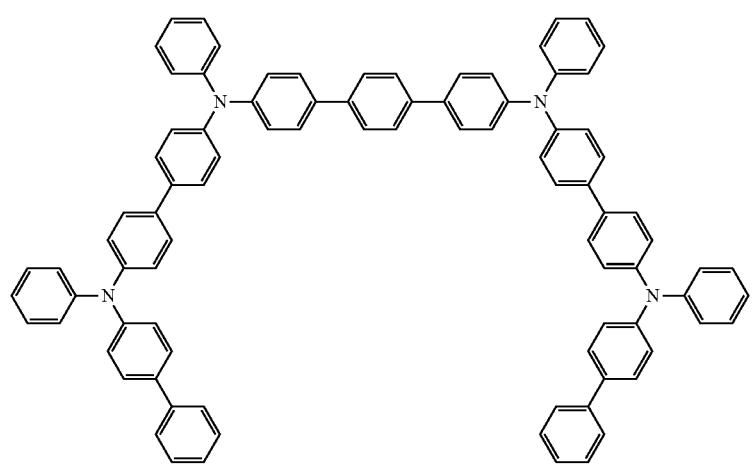 [SMILES: c1ccc(-c2ccc(N(c3ccccc3)c3ccc(-c4ccc(N(c5ccccc5)c5ccc(-c6ccc(-c7ccc(N(c8ccccc8)c8ccc(-c9ccc(N(c%10ccccc%10)c%10ccc(-c%11ccccc%11)cc%10)cc9)cc8)cc7)cc6)cc5)cc4)cc3)cc2)cc1]
Appl. Phys. Lett. 90, 183503 (2007)

TABLE 1-continued

| MATERIAL | EXAMPLES OF MATERIAL | PUBLICATIONS |
| --- | --- | --- |
|  |  | Appl. Phys. Lett. 90, 183503 (2007) |
| Triaylamine on spirofluorene core |  | Synth. Met. 91, 209 (1997) |
| Arylamine carbazole compounds |  | Adv. Mater. 6, 677 (1994) |
| Indolocarbazoles |  | Synth. Met. 111, 421 (2000) |

TABLE 1-continued

| MATERIAL | EXAMPLES OF MATERIAL | PUBLICATIONS |
|---|---|---|
| Isoindole compounds | | Chem. Mater. 15, 3148 (2003) |

Phosphorescent OLED host materials
Red hosts

| | | |
|---|---|---|
| Arylcarbazoles | | Appl. Phys. Lett. 78, 1622 (2001) |
| Metal 8-hydroxyquinolates (e.g., $Alq_3$, BAlq) | | Nature 395, 151 (1998) |
| | | US20060202194 |
| | | WO2005014551 |

TABLE 1-continued

| MATERIAL | EXAMPLES OF MATERIAL | PUBLICATIONS |
|---|---|---|
| Metal phenoxybenzothiazole compounds | | Appl. Phys. Lett. 90, 123509 (2007) |
| Conjugated oligomers and polymers (e.g., polyfluorene) | | Org. Electron. 1, 15 (2000) |

Green hosts

| | | |
|---|---|---|
| Arylcarbazoles | | Appl. Phys. Lett. 78, 1622 (2001) |
| | | US2003175553 |
| | | WO2001039234 |
| Aryltriphenylene compounds | | US20060280965 |

TABLE 1-continued
| MATERIAL | EXAMPLES OF MATERIAL | PUBLICATIONS |
|---|---|---|
| | 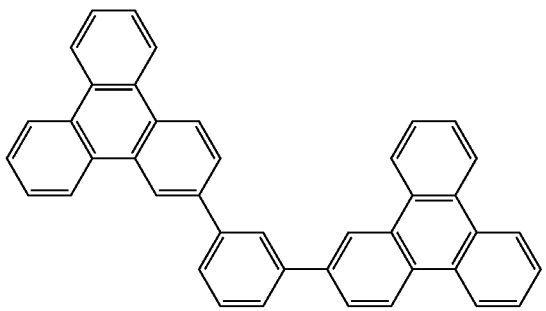 [SMILES: c1cc(-c2ccc3c4ccccc4c4ccccc4c3c2)cc(-c2ccc3c4ccccc4c4ccccc4c3c2)c1] | US20060280965 |
| Polymers (e.g., PVK) | 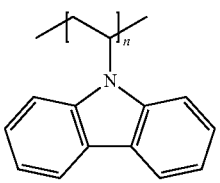 | Appl. Phys. Lett. 77, 2280 (2000) |
| Spirofluorene compounds | 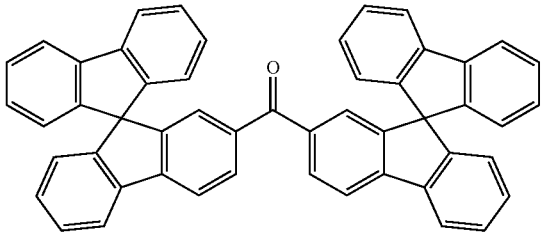 [SMILES: O=C(c1ccc2c(c1)C1(c3ccccc3-c3ccccc31)c1ccccc1-2)c1ccc2c(c1)C1(c3ccccc3-c3ccccc31)c1ccccc1-2] | WO2004093207 |
| Metal phenoxybenzooxazole compounds | 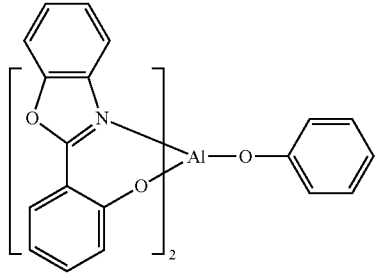 | WO05089025 |
| | 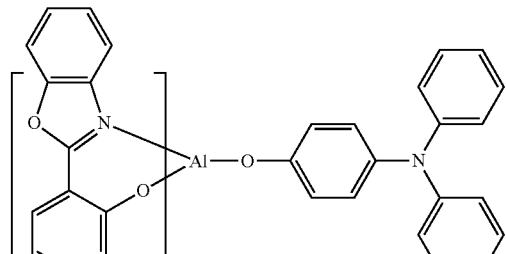 | WO06132173 |
| | 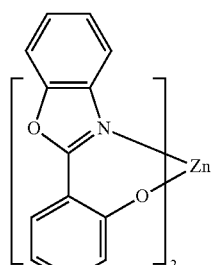 | JP200511610 |

TABLE 1-continued

| MATERIAL | EXAMPLES OF MATERIAL | PUBLICATIONS |
|---|---|---|
| Spirofluorene-carbazole compounds | | JP2007254297 |
| | | JP2007254297 |
| Indolocabazoles | | WO07063796 |
| | | WO07063754 |
| 5-member ring electron deficient heterocycles (e.g., triazole, oxadiazole) | | J. Appl. Phys. 90, 5048 (2001) |

TABLE 1-continued

| MATERIAL | EXAMPLES OF MATERIAL | PUBLICATIONS |
|---|---|---|
| | | WO04107822 |
| Metal phenoxypyridine compounds | | WO05030900 |

Blue hosts

| | | |
|---|---|---|
| Arylcarbazoles | | Appl. Phys. Lett, 82, 2422 (2003) |
| | | US20070190359 |
| Dibenzothiophene-carbazole compounds | | WO2006114966 |

TABLE 1-continued

| MATERIAL | EXAMPLES OF MATERIAL | PUBLICATIONS |
| --- | --- | --- |
| | Phosphorescent dopants | |
| | Red dopants | |
| Heavy metal porphyrins (e.g., PtOEP) | | Nature 395, 151 (1998) |
| Iridium(III) organometallic complexes | | Appl. Phys. Lett. 78, 1622 (2001) |
| | | US06835469 |
| | | US06835469 |
| | | US20060202194 |

TABLE 1-continued
| MATERIAL | EXAMPLES OF MATERIAL | PUBLICATIONS |
|---|---|---|
| | 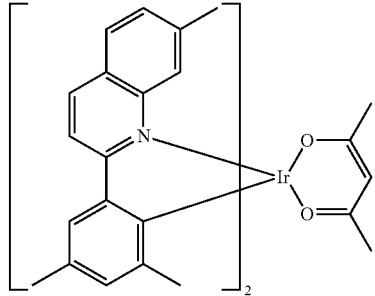 | US20060202194 |
| | 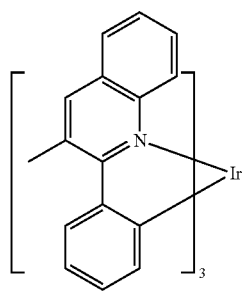 | US07087321 |
| | 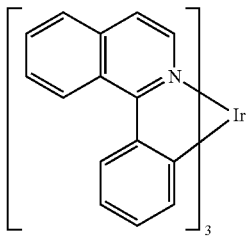 | US07087321 |
| | 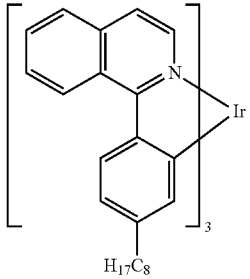 | Adv. Mater. 19, 739 (2007) |
| Platinum(II) organometallic complexes | 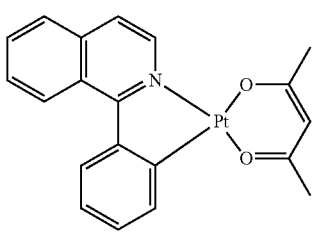 | WO2003040257 |

TABLE 1-continued

| MATERIAL | EXAMPLES OF MATERIAL | PUBLICATIONS |
| --- | --- | --- |
| Osminum(III) complexes | [structure with F₃C, pyrazole, pyridine, Os(PPhMe₂)₂]₂ | Chem. Mater. 17, 3532 (2005) |
| Ruthenium(II) complexes | [structure with tBu, pyrazole, isoquinoline, Ru(PPhMe₂)₂]₂ | Adv. Mater. 17, 1059 (2005) |

Green dopants

| MATERIAL | EXAMPLES OF MATERIAL | PUBLICATIONS |
| --- | --- | --- |
| Iridium(III) organometallic complexes | Ir(ppy)₃ structure and its derivatives | Inorg. Chem. 40, 1704 (2001) |
|  | Ir(ppy)₂(acac) structure | US2002034656 |
|  | [Ir(phenyl-benzimidazole)(acac)]₂ structure | US06687266 |

TABLE 1-continued

| MATERIAL | EXAMPLES OF MATERIAL | PUBLICATIONS |
|---|---|---|
| | | Chem. Mater. 16, 2480 (2004) |
| | | US2007190359 |
| | | US 2006008670<br>JP2007123392 |
| | | Adv. Mater. 16, 2003 (2004) |
| | | Angew. Chem. Int. Ed. 2006, 45, 7800 |

TABLE 1-continued
| MATERIAL | EXAMPLES OF MATERIAL | PUBLICATIONS |
| --- | --- | --- |
| Pt(II) organometallic complexes | 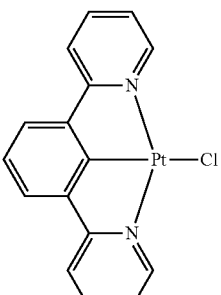 | Appl. Phys. Lett. 86, 153505 (2005) |
| | 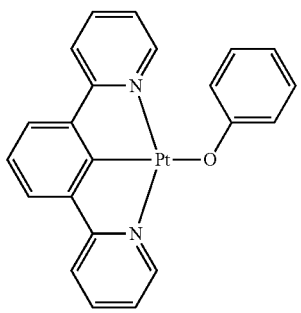 | Appl. Phys. Lett. 86, 153505 (2005) |
| | 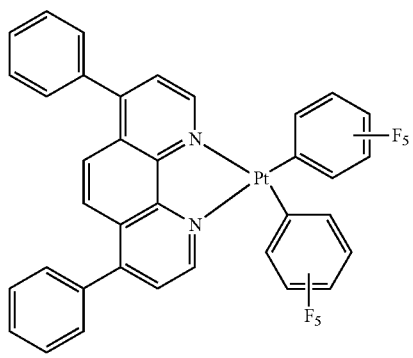 | Chem. Lett. 34, 592 (2005) |
| Gold complexes | 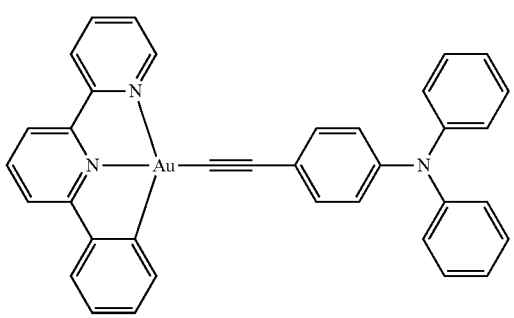 | Chem. Commun. 2906 (2005) |
| Rhenium(III) complexes | 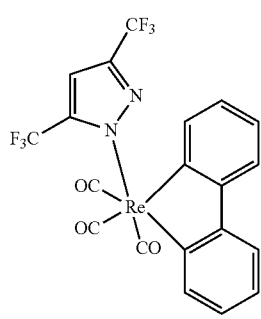 | Inorg. Chem. 42, 1248 (2003) |

TABLE 1-continued
| MATERIAL | EXAMPLES OF MATERIAL | PUBLICATIONS |
|---|---|---|
| | Blue dopants | |
| Iridium(III) organometallic complexes | 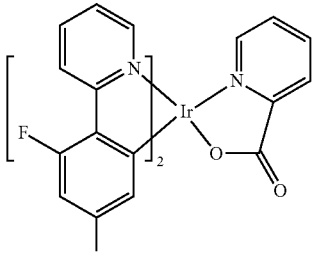 | WO2002002714 |
| | 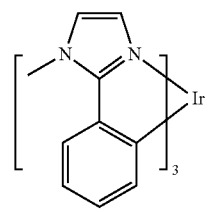 | WO2006009024 |
| | 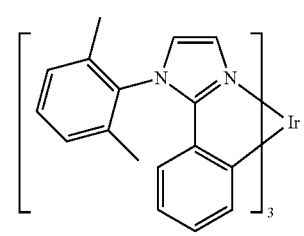 | US2006251923 |
| | 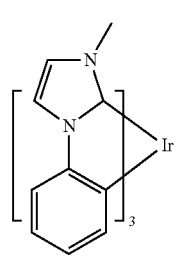 | WO2006056418, US2005260441 |
| | 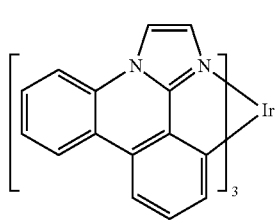 | US2007190359 |
| | 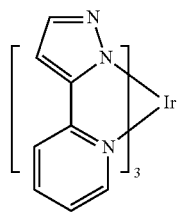 | US2002134984 |

TABLE 1-continued

| MATERIAL | EXAMPLES OF MATERIAL | PUBLICATIONS |
| --- | --- | --- |
|  |  | Angew. Chem. Int. Ed. 47, 1 (2008) |
|  |  | Chem. Mater. 18, 5119 (2006) |
|  |  | Inorg. Chem. 46, 4308 (2007) |
|  |  | WO05123873 |
|  |  | WO05123873 |
|  |  | WO07004380 |

TABLE 1-continued
| MATERIAL | EXAMPLES OF MATERIAL | PUBLICATIONS |
|---|---|---|
| | 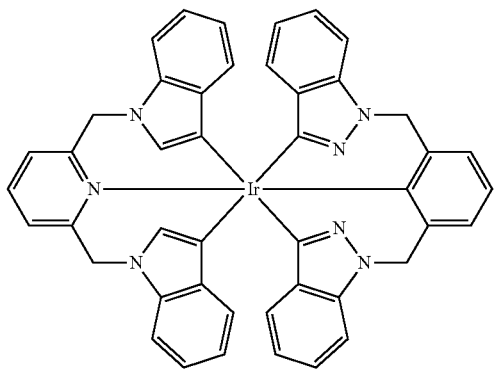 | WO06082742 |
| Osmium(II) complexes | 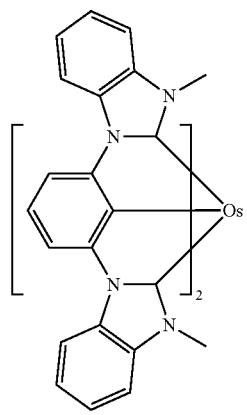 | US2005260449 |
| | 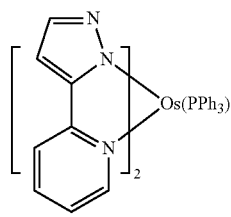 | Organometallics 23, 3745 (2004) |
| Gold complexes | 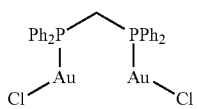 | Appl. Phys. Lett. 74, 1361 (1999) |
| Platinum(II) complexes | 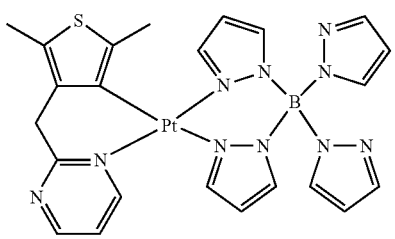 | WO06098120, WO06103874 |

TABLE 1-continued

| MATERIAL | EXAMPLES OF MATERIAL | PUBLICATIONS |
|---|---|---|
| Exciton/hole blocking layer materials | | |
| Bathocuprine compounds (e.g., BCP, BPhen) | 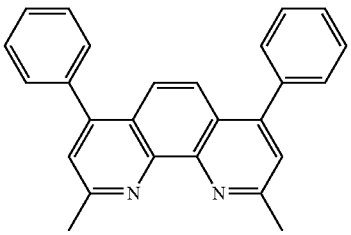 [SMILES: Cc1cc(-c2ccccc2)c2ccc3c(-c4ccccc4)cc(C)nc3c2n1] | Appl. Phys. Lett. 75, 4 (1999) |
| | 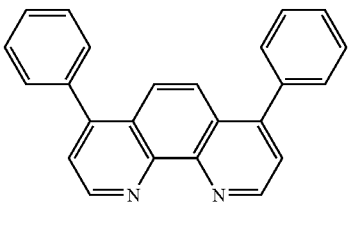 [SMILES: c1ccc(-c2ccnc3c2ccc2c(-c4ccccc4)ccnc23)cc1] | Appl. Phys. Lett. 79, 449 (2001) |
| Metal 8-hydroxyquinolates (e.g., BAlq) | 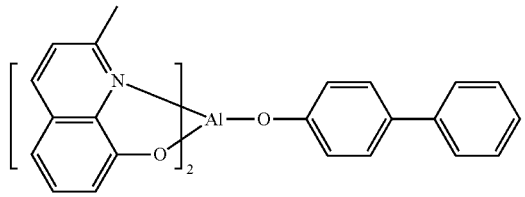 | Appl. Phys. Lett. 81, 162 (2002) |
| 5-member ring electron deficient heterocycles such as triazole, oxadiazole, imidazole, benzoimidazole | 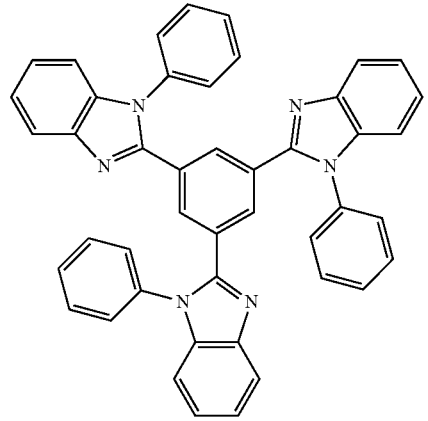 [SMILES: c1ccc(-n2c(-c3cc(-c4nc5ccccc5n4-c4ccccc4)cc(-c4nc5ccccc5n4-c4ccccc4)c3)nc3ccccc32)cc1] | Appl. Phys. Lett. 81, 162 (2002) |
| Triphenylene compounds | 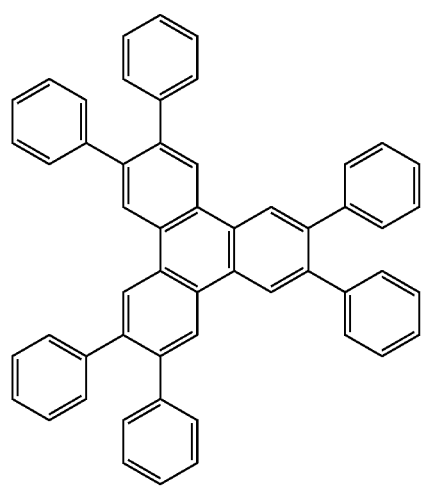 [SMILES: c1ccc(-c2cc3c4cc(-c5ccccc5)c(-c5ccccc5)cc4c4cc(-c5ccccc5)c(-c5ccccc5)cc4c3cc2-c2ccccc2)cc1] | US20050025993 |

TABLE 1-continued

| MATERIAL | EXAMPLES OF MATERIAL | PUBLICATIONS |
|---|---|---|
| Fluorinated aromatic compounds | | Appl. Phys. Lett. 79, 156 (2001) |

Electron transporting materials

| | | |
|---|---|---|
| Anthracene-benzoimidazole compounds | | WO03060956 |
| Anthracene-benzothiazole compounds | | Appl. Phys. Lett. 89, 063504 (2006) |
| Metal 8-hydroxyquinolates (e.g., $Alq_3$) | | Appl. Phys. Lett. 51, 913 (1987) |

TABLE 1-continued

| MATERIAL | EXAMPLES OF MATERIAL | PUBLICATIONS |
| --- | --- | --- |
| Metal hydroxybenoquinolates | | Chem. Lett. 5, 905 (1993) |
| Bathocuprine compounds such as BCP, BPhen, etc | | Appl. Phys. Lett. 91, 263503 (2007) |
| | | Appl. Phys. Lett. 79, 449 (2001) |
| 5-member ring electron deficient heterocycles (e.g.,triazole, oxadiazole, imidazole, benzoimidazole) | | Appl. Phys. Lett. 74, 865 (1999) |
| | | Appl. Phys. Lett. 55, 1489 (1989) |
| | | Jpn. J. Apply. Phys. 32, L917 (1993) |

| MATERIAL | EXAMPLES OF MATERIAL | PUBLICATIONS |
|---|---|---|
| Silole compounds | 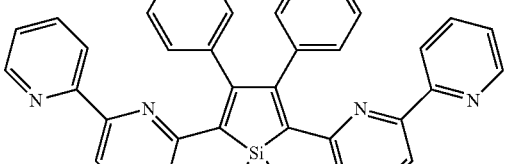 | Org. Electron. 4, 113 (2003) |
| Arylborane compounds | 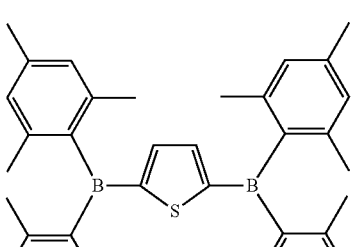 | J. Am. Chem. Soc. 120, 9714 (1998) |
| Fluorinated aromatic compounds | 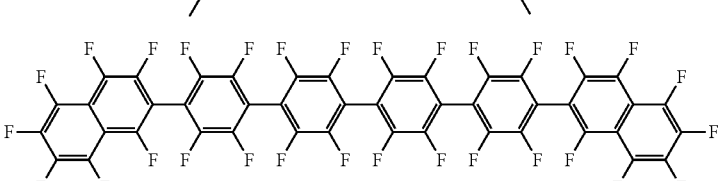 | J. Am. Chem. Soc. 122, 1832 (2000) |

EXPERIMENTAL

Compound Examples

Several of the compounds were synthesized as follows:

Example 1

Synthesis of Compound 1

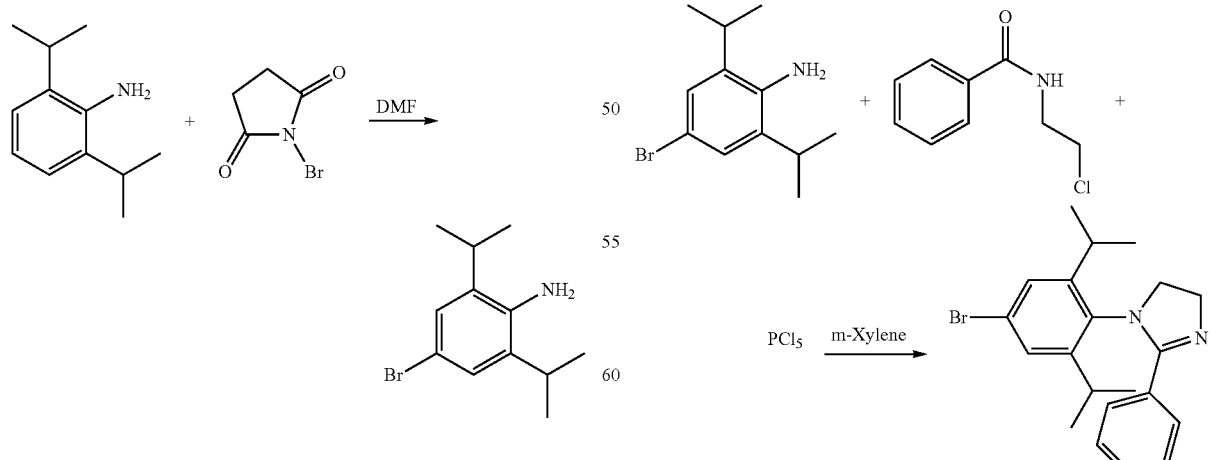

Into a 1000 mL three-neck flask was placed 2,6-diisopropylaniline (35 g, 0.197 mol) followed by 150 mL of DMF. Next, N-Bromosuccinimide (35 g, 0.197 mol) dissolved in 100 mL of DMF was added dropwise to the solution of the aniline. The internal temperature was maintained between 25-30° C. during the addition of the N-Bromosuccinimide. Stirring was continued overnight. The reaction mixture was worked up by diluting with aqueous sodium bicarbonate then was extracted 3×150 mL ethyl acetate. The extracts were combined and washed 3×100 mL aqueous 10% LiCl. The extracts were then dried over magnesium sulfate, filtered and stripped under vacuum. Silica gel chromatography of the crude product (30-50% methylene chloride/hexanes) yielded 26 g (50% yield) of product.

Into a 1000 mL three-neck flask was placed N-(2-chloroethyl)benzamide (17.6 g, 0.095 mol), Phosphorus pentachloride (30.6 g, 0.147 mol) and 200 mL of m-Xylene. This mixture was stirred and heated at 130° C. for 90 min. The reaction mixture was cooled to room temperature and 4-Bromo-2,6-diisopropylaniline (23.4 g, 0.091 mol) was dissolved in 20 mL of m-Xylene and was added all at once to the reaction mixture. This mixture was heated back up to 130° C. and was maintained at this temperature for 18 h. For the work-up, the reaction mixture was cooled to 0-5° C. and was stirred at this temperature for an hour. A solid was collected via filtration. This solid was then basified using aqueous sodium hydroxide. The basic aqueous was extracted 3×200 mL ethyl acetate. These extracts were dried over magnesium sulfate, then were filtered and stripped under vacuum yielding 28 g (80% yield) of product.

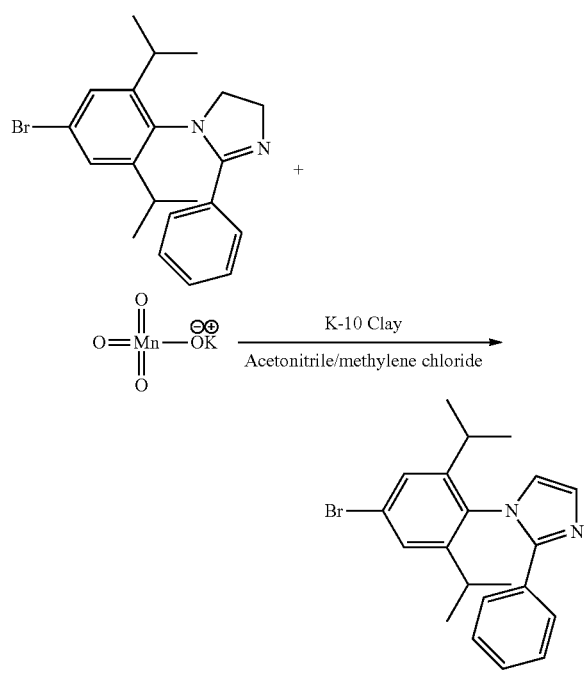

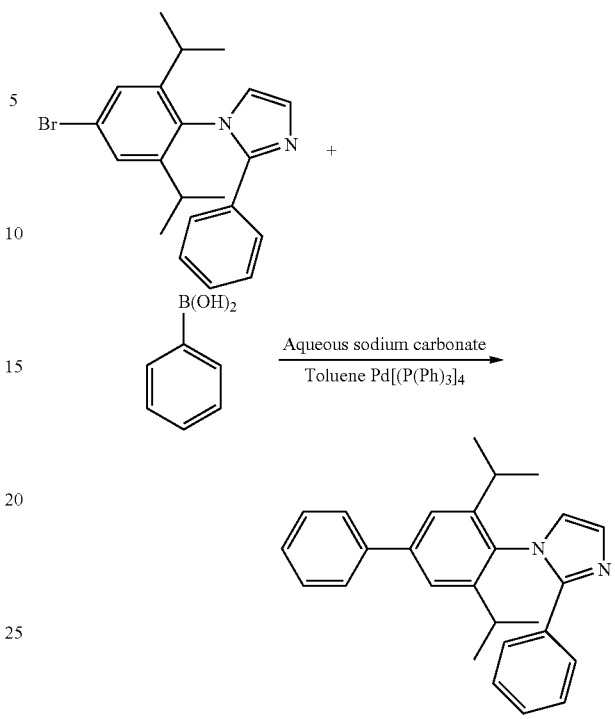

Potassium permanganate (13.13 g, 0.083 mol) and 26 g of Montmorillonite K-10 were ground together using a mortar and pestle. Next, the imidazoline (16 g, 0.042 mol) was charged into a 500 mL 3-neck flask with 200 mL of acetonitrile and 75 mL of methylene chloride. The potassium permanganate/K-10 mixture was added portionwise over a 20 min period to the reaction mixture. The internal temperature rose to 35-38° C. during the addition of the oxidant. The reaction mixture was stirred for 90 min after the oxidant addition was complete. The internal temperature fell back down to 22-23° C. The reaction mixture was quenched by adding ethanol (80 mL) all at once. This mixture was stirred for 1 h at room temperature. The mixture was then filtered through a pad of Celite and the filtrate was stripped under vacuum. The crude product was first purified by silica gel chromatography (2-10% acetone/methylene chloride) and second using neutral alumina chromatograpy using 40-90% methylene chloride/hexanes as the eluent. The neutral alumina was deactivated before use by adding 6% water (w/w). After chromatography, 8.5 g (53% yield) of product was obtained.

Phenyl boronic acid (3.26 g, 0.027 mol) and the bromo imidazole (6.6 g, 0.0172 mol) were charged into a 500 mL round bottom flask with 200 mL of toluene. Next, Sodium carbonate (8.5 g, 0.08 mol) was dissolved in 35 mL of water and was added to the reaction mixture. Lastly, Tetrakis(triphenylphosphine)palladium(0) (1.35 g, 0.0012 mol) was added to the reaction mixture. This reaction mixture was evacuated and back-filled with nitrogen (this procedure repeated several times). The reaction mixture was then stirred and heated at reflux for 18 h. The reaction mixture was cooled to room temperature. The toluene layer was separated from the aqueous layer. The aqueous layer was extracted 1×50 mL toluene. The toluene extracts were combined, dried over magnesium sulfate, filtered and stripped under vacuum. The crude product was first purified by silica gel chromatography (10-20% ethyl acetate/methylene chloride). The cleanest product fractions were combined and stripped under vacuum. This material was stirred overnight in 100 mL of methylene chloride with 0.75 g of Si-TAACOH and 0.75 g of Siliabond DMT. This procedure is to remove residual palladium. This mixture was then filtered and stripped under vacuum yielding 5.95 g of product. This material was then dissolved in 75 mL of THF and was cooled to −78° C. To this cooled reaction mixture was added 13 mL of 1.6 M n-BuLi over a 5 min period. The mixture was then stirred for an additional 5 min at −78° C. This mixture was then quenched with 50 mL of water and was extracted 2×100 mL ethyl acetate. The ethyl acetate extracts were dried over magnesium sulfate filtered and stripped under vacuum. This material was again purified by silica gel chromatography followed by hexane recrystallizations. A total of 4.6 g (70% yield) of product was obtained.

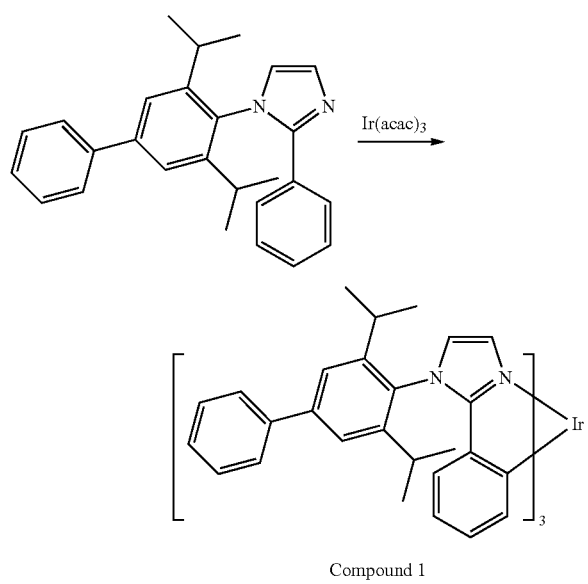

Compound 1

Synthesis of Compound 1

A 50 mL Schlenk tube flask was charged with N-(2,6-diisopropyl-4-phenyl phenyl)-2-phenylimidazole (4.6 g, 12.1 mmol), tris(acetylacetonate) iridium(III) (1.2 g, 2.4 mmol) and tridecane (1 mL). The reaction mixture was stirred under a nitrogen atmosphere and heated at 240° C. for 48 h. After cooling, the solidified mixture was washed first with absolute ethanol followed by hexane. The residue was further purified by a silica gel column to give fac-tris[N-(2,6-diisopropyl-4-phenyl phenyl)-2-phenylimidazole]iridium(III) (2.0 g). The product was further purified by vacuum sublimation.

Example 2

Synthesis of Compound 2

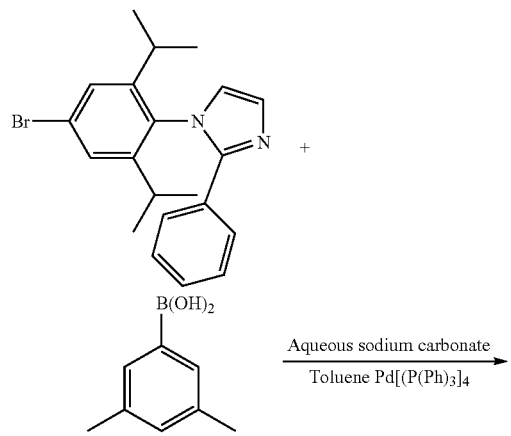

3,5-Dimethylphenyl boronic acid (4.05 g, 0.027 mol) and the bromo imidazole (6.5 g, 0.017 mol) were charged into a 500 mL round bottom flask with 200 mL of toluene. Next, Sodium carbonate (8.5 g, 0.08 mol) was dissolved in 35 mL of water and was added to the reaction mixture. Lastly, Tetrakis (triphenylphosphine)palladium(0) (1.35 g, 0.0012 mol) was added to the reaction mixture. This reaction mixture was evacuated and back-filled with nitrogen (this procedure repeated several times). The reaction mixture was then stirred and heated at reflux for 18 h. The reaction mixture was cooled to room temperature. The toluene layer was separated from the aqueous layer. The aqueous layer was extracted 1×50 mL toluene. The toluene extracts were combined, dried over magnesium sulfate, filtered and stripped under vacuum. The product was purified the same as the above material. After one recrystallization, 4.45 g (64% yield) of product was obtained.

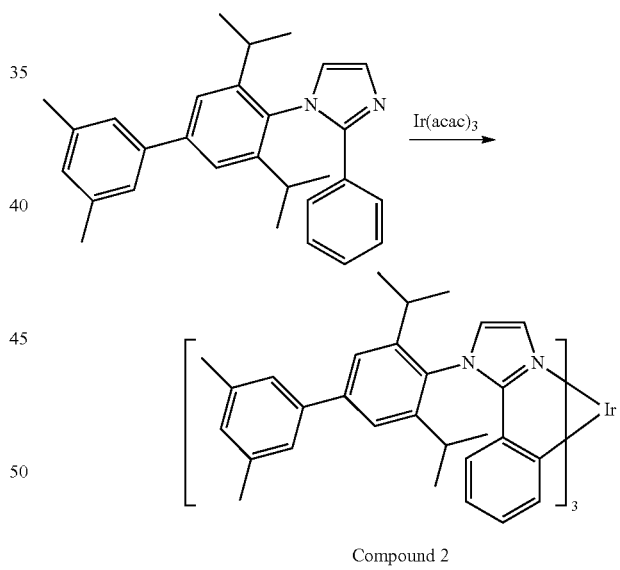

Compound 2

Synthesis of Compound 2

A 50 mL Schlenk tube flask was charged with N-(2,6-diisopropyl-4-(3,5-dimethylphenyl) phenyl)-2-phenylimidazole (4.4 g, 10.8 mmol), tris(acetylacetonate)iridium(III) (1.1 g, 2.2 mmol), and tridecane (1 mL). The reaction mixture was stirred under a nitrogen atmosphere and heated at 240° C. for 48 h. After cooling, the solidified mixture was washed first with absolute ethanol followed by hexane. The residue was further purified by a silica gel column to give fac-tris[N-(2, 6-diisopropyl-4-(3,5-dimethylphenyl)phenyl)-2-phenylimidazole]iridium(III) (2.2 g). The product was further purified by vacuum sublimation.

Example 3

Synthesis of Compound 3

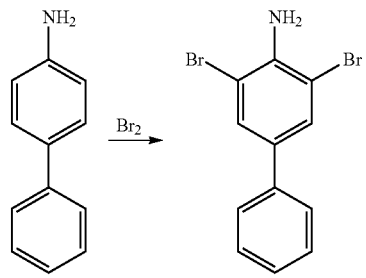

Synthesis of 3,5-dibromobiphenyl-4-amine. To a solution of 4-aminobiphenyl (8.6 g, 0.050 mol) in acetic acid (250 mL) was added, dropwise, a solution of bromine (16.0 grams, 0.100 mol) in acetic acid (70 mL). The resulting suspension was stirred at ambient temperature for 3 h before being poured into ice-water (500 mL). The solid was filtered, washed with water and dissolved in dichloromethane. After washing with water, the organic layer was dried (sodium sulfate), filtered and evaporated. The crude solid was chromatographed (silica gel) using a mobile phase of hexane-dichloromethane 3:1 to give 12.56 grams (77% yield) of the product as a white solid. GC-MS confirmed structure.

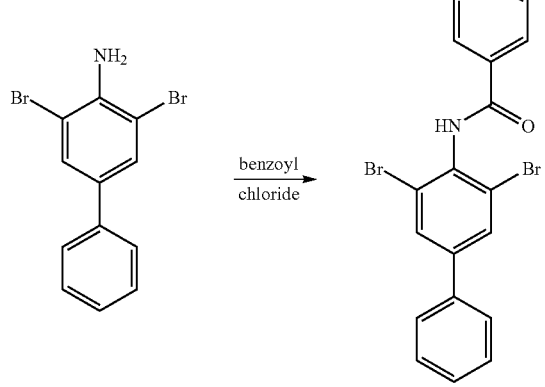

Synthesis of N-(3,5-dibromobiphenyl-4-yl)benzamide

Benzoyl chloride (4.0 mL, 0.035 mol) was added to a solution of 3,5-dibromobiphenyl-4-amine (10.5 g, 0.032 mol) in pyridine (75 mL). This was stirred for 16 h before being poured into water. The crude solid was filtered, washed with water and chromatographed (silica gel). The column was eluted first with hexanes and dichloromethane (1:1) then dichloromethane to afford the product as a white solid.

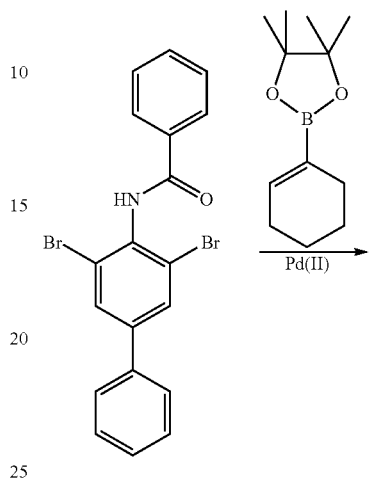

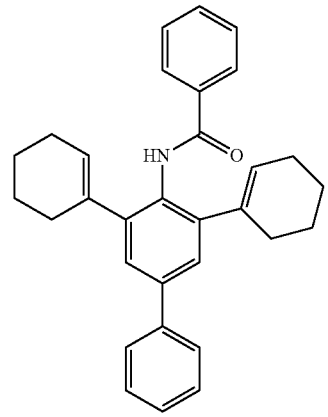

Synthesis of N-(3,5-dicyclohexenyl-4-yl)benzamide

Into a 1 L 3-neck flask were placed N-(3,5-dibromobiphenyl-4-yl)benzamide (4.19 g, 9.70 mmol), cyclohexene-1-boronic acid pinacol ester (10.1 g, 48.0 mmol), palladium acetate (0.24 g, 1.0 mmol), 2-dicyclohexylphosphino-2',6'-dimethoxybiphenyl (0.88 g, 2.00 mmol), potassium phosphate monohydrate (11.1 g, 48.0 mmol), toluene (170 mL) and water (170 mL). The mixture was purged with nitrogen for 30 min before being stirred at reflux for 16 h. The mixture was then diluted with water (150 mL). The layers were separated and the aqueous layer was extracted with ethyl acetate. The combined organic layers were washed with water, dried (sodium sulfate) and concentrated. Flash chromatography with dichloromethane and hexanes (1:1) then dichloromethane yielded 3.56 grams (85% yield) of the product as a white solid. $^1$H NMR confirmed the structure.

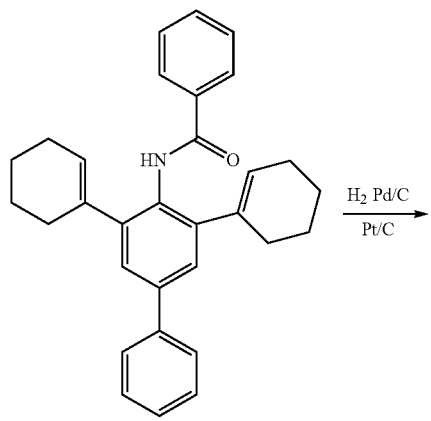

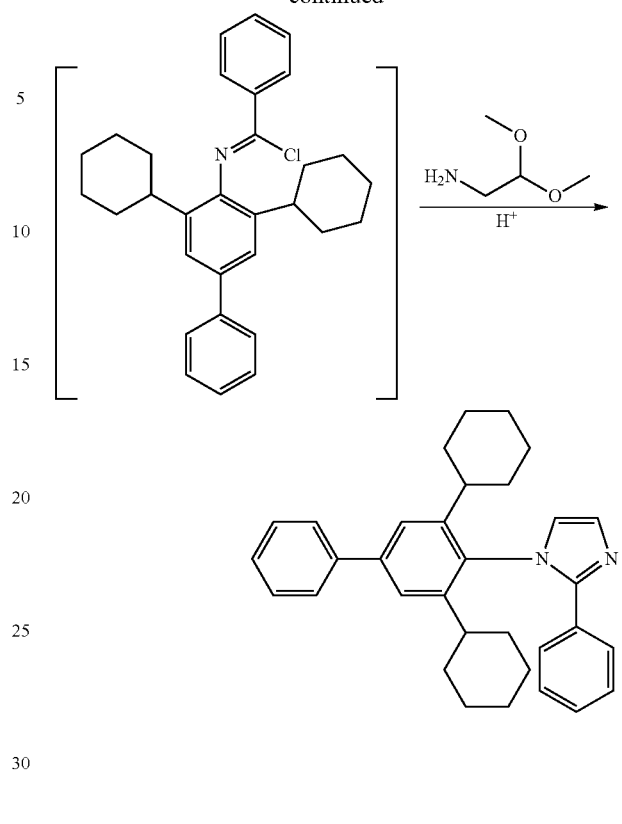

Synthesis of N-(3,5-dicyclohexyl-4-yl)benzamide

Into a Parr hydrogenation bottle were placed N-(3,5-dicyclohexenyl-4-yl)benzamide (2.0 g, 4.6 mmol), anhydrous tetrahydrofuran (200 mL), Palladium on Carbon 10% (2.0 grams) and Platinum, 5 wt. % on activated carbon, wet, Degussa type F101 RA/W (2.0 grams). This was shaken under 45 psi for 16 h. The mixture was then filtered through celite and the filtrate evaporated to give 2.0 g (99% yield) of the product as a white solid. GC-MS confirmed the structure.

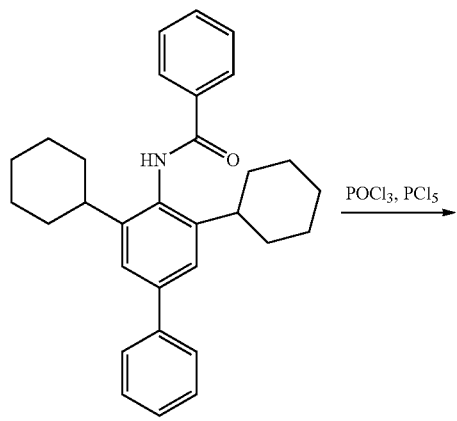

Synthesis of 1-(3,5-dicyclohexylbiphenyl-4-yl)-2-phenyl-1H-imidazole

A mixture of N-(3,5-dicyclohexyl-4-yl)benzamide (2.1 g, 4.8 mmol), phosphorus oxychloride (10 mL) and phosphorus pentachloride (1.0 g, 4.8 mmol) was stirred at reflux for 4 h. The phosphorous oxychloride was removed in vacuo. To the crude brown solid was added 25 mL of isopropanol and aminoacetaldehyde dimethyl acetal (10.4 mL, 96.0 mmol). This was stirred at ambient temperature for 22 h. The mixture was concentrated on the rotary evaporator. To the residue was added a mixture of 30 mL of isopropanol and 30 mL of con HCl. This was stirred at 90° C. for 22 h. The mix was then cooled to ambient temperature and the pH was adjusted to 10 using 1N NaOH. The product was extracted with dichloromethane and purified on a silica gel column. Elution with dichloromethane and ethyl acetate (95:5) yielded 1.4 grams (64%) of the product. $^1$H NMR confirmed the structure.

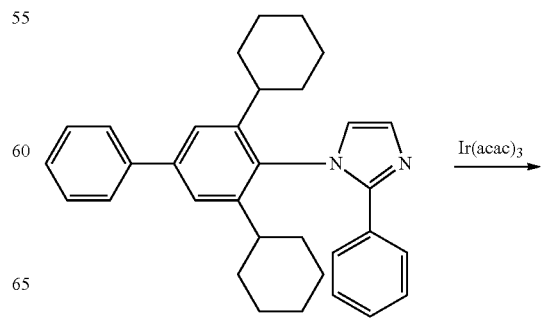

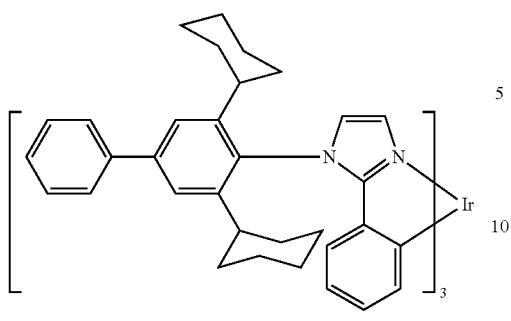

Compound 3

Synthesis of Compound 3

Into a Schlenk tube were added a stir bar, 1-(3,5-dicyclohexylbiphenyl-4-yl)-2-phenyl-1H-imidazole (3.1 grams, 6.7 mmol), iridium (III) acetylacetonate (0.66 grams, 1.3 mmol) and tridecane (0.3 mL). This was evacuated and backfilled with nitrogen. The reaction was stirred at 250° C. for 48 h. The product was purified using column chromatography. Elution with hexanes and dichloromethane (1:1) gave 1.88 grams (92%) of the product as a yellow solid. $^1$H NMR confirmed structure.

Example 4

Synthesis of Compound 4

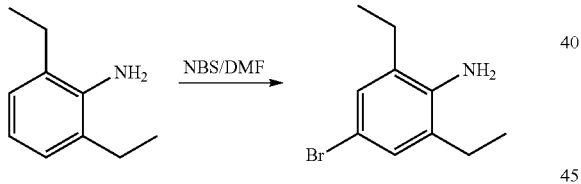

Synthesis of 4-bromo-2,6-diethylaniline. 2,6-diethylaniline (7 g, 46.9 mmol) was dissolved in 50 mL of DMF in a round-bottom flask and cooled with an ice-water bath. N-bromosuccimide (NBS) (9.18 g, 51.6 mmol) was dissolved in 100 mL of DMF and added dropwise to the flask via a dropping funnel. The reaction was warmed slowly to room temperature and reacted overnight before it was quenched by ice water. The product was extracted with dichloromethane and washed with lithium chloride solution. After evaporating solvent, the residue was purified by silica gel column chromatography. 5.5 g (51.4% yield) of product was obtained.

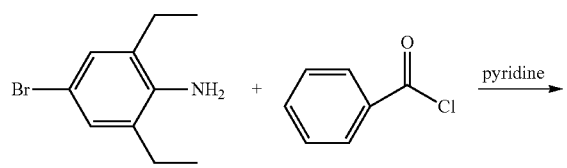

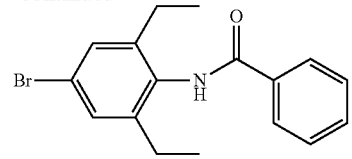

Synthesis of N-(4-bromo-2,6-diethylphenyl)benzamide

A solution of 4-bromo-2,6-diethylaniline (5.48 g, 24 mmol) in dichloromethane was added and stirred under nitrogen. Pyridine (5.7 g, 72.1 mmol) was added followed by benzoyl chloride (4.39 g, 31.2 mmol). The reaction was stirred for 1 h. The reaction was diluted with dichloromethane, washed with 10% sodium hydroxide solution, 1N HCl, and dried over magnesium sulfate, filtered, and evaporated. The residue was pre-absorbed onto Celite and purified by column chromatography. The column was eluted with 40 to 100% dichloromethane/hexanes. 7.64 g (96% yield) of product was obtained after purification.

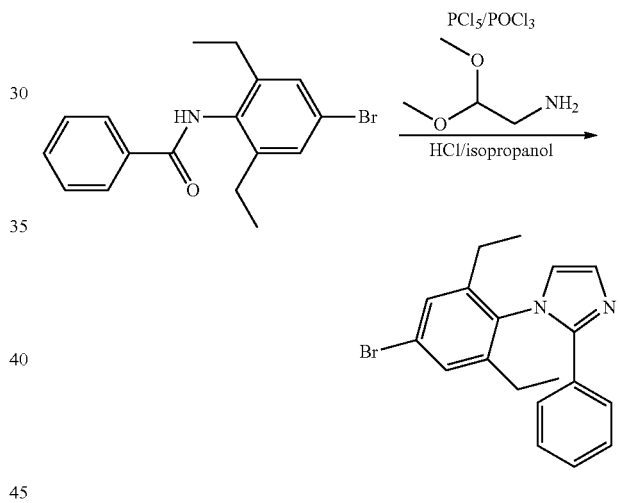

Synthesis of 1-(4-bromo-2,6-diethylphenyl)-2-phenyl-1H-imidazole

In a 250 mL round-bottom flask added N-(4-bromo-2,6-diethylphenyl)benzamide (7.64 g, 23 mmol), phosphorus pentachloride (4.79 g, 23 mmol), and phosphorus oxychloride (40 mL). The reaction was heated up to reflux under nitrogen. After 2.5 h, the reaction mixture was cooled and phosphorus oxychloride was distilled off using short path distillation apparatus. 2-propanol (40 mL) and 2,2-dimethoxyethanamine (48.4 g, 460 mmol) was added. The reaction was stirred at room temperature for 4 h. Concentrated hydrochloric acid (40 mL) was added carefully, and the reaction was heated to reflux overnight. The solution was decanted from black solid and neutralized with 10% sodium hydroxide solution, extracted with ethyl acetate. The organic layers were dried over magnesium sulfate. The residue was purified by silica gel column chromatography eluting with 20 and 30% ethyl acetate/hexanes. 6.75 g (83% yield) of product was obtained after purification.

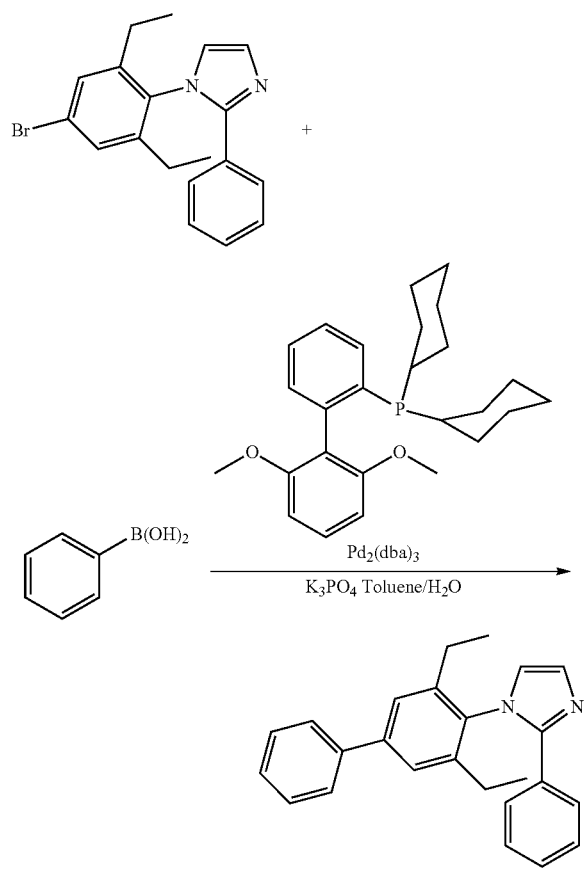

Synthesis of 1-(3,5-diethylbiphenyl-4-yl)-2-phenyl-1H-imidazole

A 2-necked 250 mL round-bottom flask was charged with 1-(4-bromo-2,6-diethylphenyl)-2-phenyl-1H-imidazole (6.75 g, 19 mmol), phenylboronic acid (4.63 g, 38 mmol), dicyclohexyl (2',6'-dimethoxy-biphenyl-2-yl)phosphine (0.312 g, 0.76 mmol), and tripotassium phosphate monohydrate (12.1 g, 51 mmol) in 100 mL of toluene and 10 mL of water. The mixture was degassed by bubbling nitrogen directly into solution for 20 min. Pd$_2$(dba)$_3$ was added and the reaction heated to reflux overnight under nitrogen. The organic layer was separated and solvent was evaporated. The material was column purified by silica gel chromatography eluting with 20% ethyl acetate/hexanes. 5.5 g (82% yield) of product was obtained.

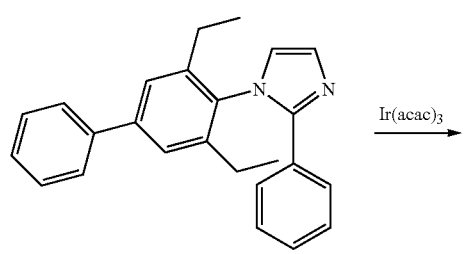

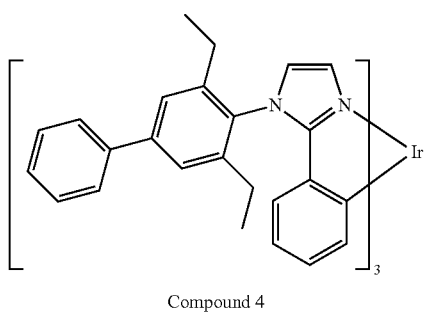

Compound 4

Synthesis of Compound 4

1-(3,5-diethylbiphenyl-4-yl)-2-phenyl-1H-imidazole (4 g, 11.35 mmol) and tris(acetylacetonate)iridium (III) (1.111 g, 2.270 mmol) were added to a Schlenck tube. 0.5 mL of tridecance was added. The reaction flask was evacuated and backfilled with nitrogen. The process was repeated for 3 times. The reaction was heated up to 250° C. under nitrogen for 48 h. After completion, the reaction mixture was diluted with dichloromethane and hexanes. The solution was concentrated under reduced pressure. 200 mL of hexanes was added. The solid was then collected by filtration. The solid was dissolved in dichloromethane and coated on Celite. The residue was purified with silica gel column chromatography using 1:1 DCM/hexanes. 1.2 g (42.4% yield) of product was obtained after purification.

Example 5

Synthesis of Compound 5

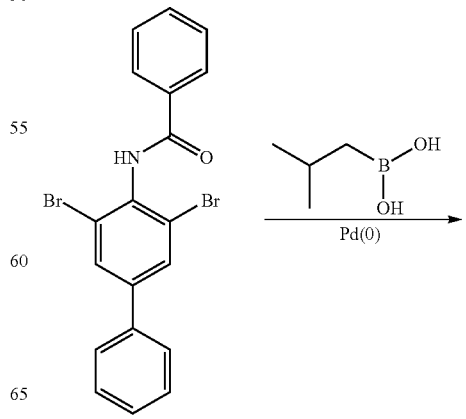

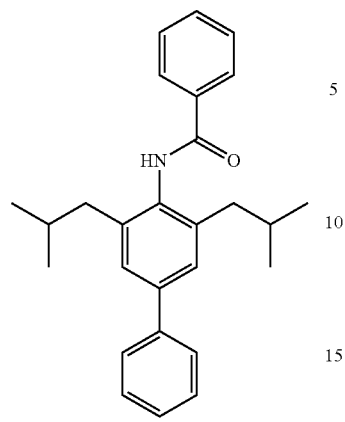

Synthesis of N-(3,5-diisobutylbiphenyl-4-yl)benzamide

A mixture of N-(3,5-dibromobiphenyl-4-yl)benzamide (8.52 g, 19.8 mmol), isobutyl boronic acid (8.06 g, 79.2 mmol), potassium phosphate monohydrate (13.7 g, 59.4 mmol), water. (50 mL) and toluene (150 mL) was purged with nitrogen for 20 min before addition of tris(dibenzylideneacetone) dipalladium(0) (0.27 g 3% Pd) and 2-dicyclohexylphosphino-2',6'-dimethoxybiphenyl (0.49 g, 6 mol %). The reaction was stirred at reflux for 18 h. After cooling to ambient temperature the mixture was diluted with ethyl acetate and water. The layers were separated and the organic layer was concentrated and chromatographed on a silica gel column. Elution first with dichloromethane then dichloromethane and ethyl acetate (49:1) gave 6.53 g (86% yield) of the desired product as a solid. $^1$H NMR confirmed the structure.

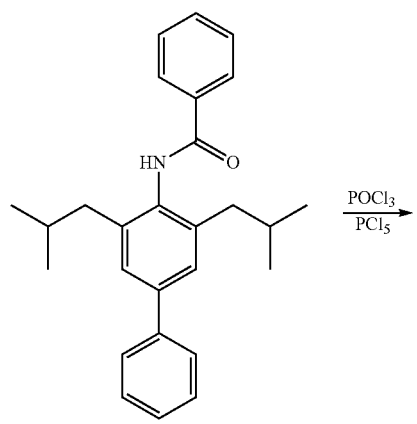

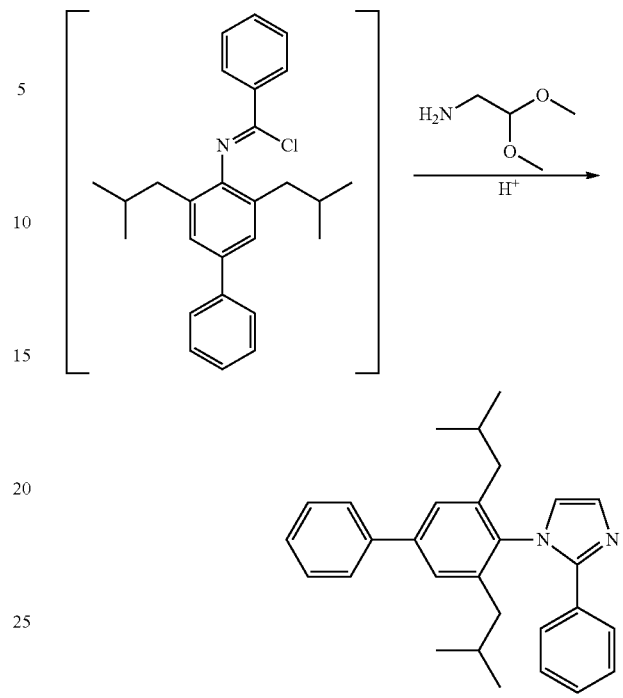

Synthesis of 1-(3,5-diisobutylbiphenyl-4-yl)-2-phenyl-1H-imidazole

A mixture of N-(3,5-diisobutylbiphenyl-4-yl)benzamide (6.27 g, 16.3 mmol), phosphorus oxychloride (20 mL), and phosphorus pentachloride (3.40 g, 16.3 mmol) was stirred at reflux for 4 h. The phosphorus oxychloride was removed by vacuum distillation. To the crude imidoyl chloride was added isopropanol (40 mL) and aminoacetaldehyde dimethyl acetal (35 mL, 321 mmol). This was stirred at ambient temperature for 18 h after which time conc. HCl (75 mL) was added. This was stirred at reflux for 18 h. The mixture was neutralized with 1N NaOH to pH 9 and extracted with dichloromethane. The product was purified on a silica gel column. Elution first with dichloromethane then dichloromethane and ethyl acetate (9:1) gave the desired product which was recrystallized from hexane to give 3.64 g (55% yield) as a white solid. Structure was confirmed by LC-MS and $^1$H NMR.

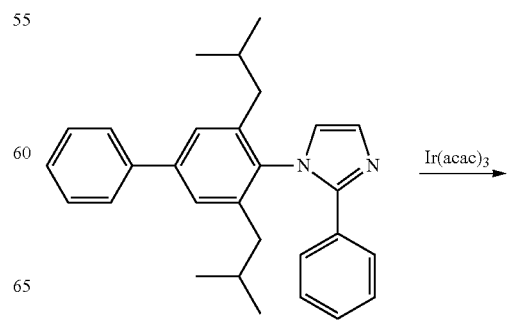

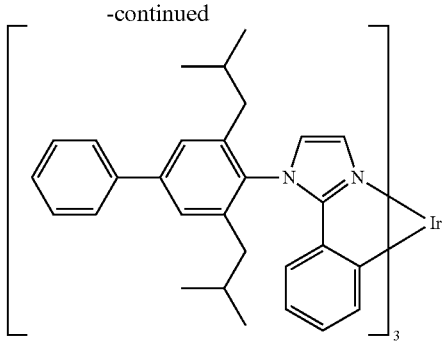

Compound 5

Synthesis of Compound 5

1-(3,5-diisobutylbiphenyl-4-yl)-2-phenyl-1H-imidazole (3.64 g, 8.91 mmol), iridium (III) acetylacetonate (0.88 g, 1.78 mmol) and tridecane (42 drops) were placed in a Schlenk tube. The tube was evacuated and backfilled with nitrogen and the mixture was then stirred at 250° C. for 48 h. The product was extracted with dichloromethane and purified on a silica gel column. Elution with dichloromethane and hexane (1:1) afforded 1.02 g (40%) of product. $^1$H NMR confirmed the structure.

Example 6

Synthesis of Compound 6

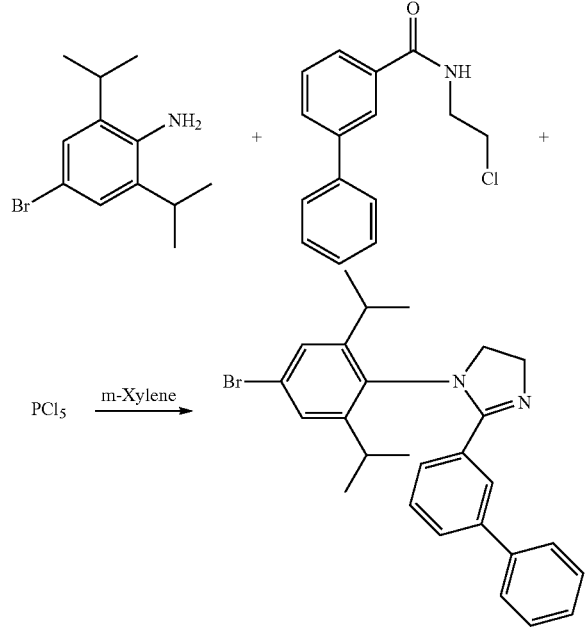

Into a 1000 mL three-neck flask was placed N-(2-chloroethyl)phenylbenzamide (18.0 g, 0.0693 mol), Phosphorus pentachloride (21.65 g, 0.104 mol) and 200 mL of m-Xylene. This mixture was stirred and heated at 130° C. for 90 min. The reaction mixture was cooled to room temperature and 4-Bromo-2,6-diisopropylaniline (19.53 g, 0.07623 mol) was dissolved in 20 mL of m-Xylene and this mixture was added all at once to the reaction. This mixture was heated back up to 130° C. and was maintained at this temperature for 18 h. For the work-up, the reaction mixture was cooled to 0-5° C. and was stirred at this temperature for an hour. A solid was collected via filtration. This solid was then basified using aqueous sodium hydroxide. The basic aqueous was extracted 3×200 mL ethyl acetate. These extracts were dried over magnesium sulfate, then were filtered and stripped under vacuum yielding 10 g of product.

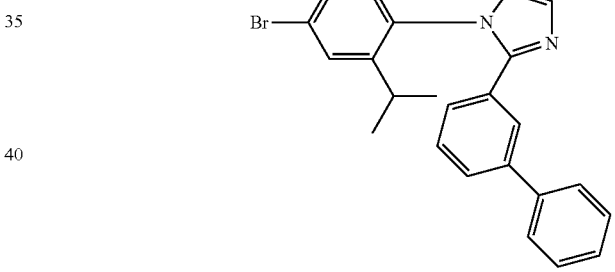

Potassium permanganate (6.85 g, 0.04334 moles) and 14 g of Montmorillonite K-10 were ground together using a mortar and pestle. Next, the imidazoline (10.00 g, 0.0217 mol) was charged into a 500 mL 3-neck flask with 200 mL of acetonitrile and 50 mL of methylene chloride. The potassium permanganate/K-10 mixture was added portion-wise over a 20 min period to the reaction mixture. The internal temperature was rose to 20-25° C. during the addition of the oxidant. The reaction mixture was stirred for 90 min after the oxidant addition was complete. The internal temperature fell back down to 22-23° C. The reaction mixture was quenched by adding ethanol (50 mL) all at once. This mixture was stirred for 1 h at room temperature. The mixture was then filtered through a pad of Celite and the filtrate was stripped under vacuum. The crude product was first purified by silica gel chromatography (5-10% Ethyl acetate/methylene chloride). This crystallized from ethyl acetate—Hexane, and gave 4.5 g product.

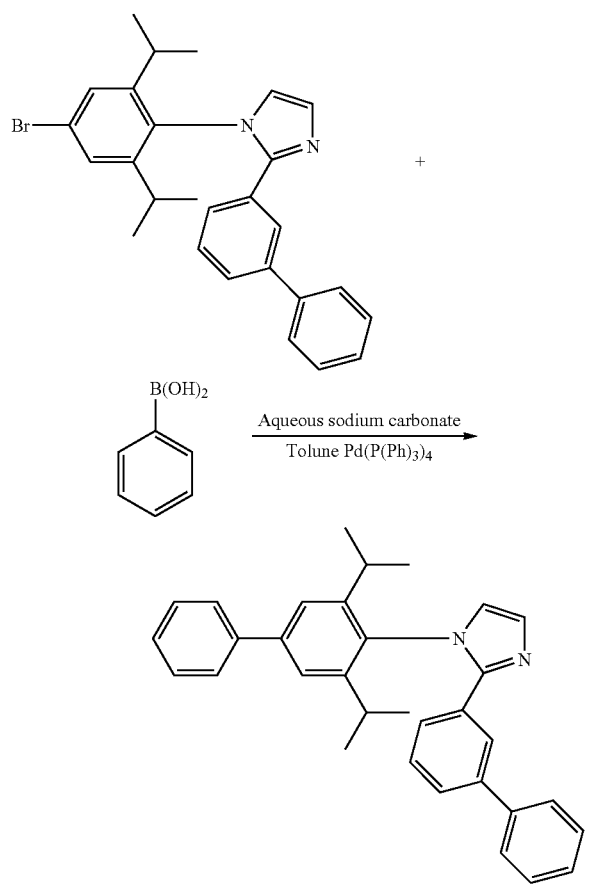

Phenyl boronic acid (1.91 g, 0.0156 mol) and the bromo imidazole (4.5 g, 0.0098 mol) were charged into a 500 mL round bottom flask with 150 mL of toluene. Next, Sodium carbonate (3.11 g, 0.0294 mol) was dissolved in 20 mL of water and was added to the reaction mixture. Lastly, Tetrakis (triphenylphosphine)palladium(0) (0.792 g, 0.00069 moles) was added to the reaction mixture. This reaction mixture was evacuated and back-filled with nitrogen (this procedure repeated several times). The reaction mixture was then stirred and heated at reflux for 18 h. The reaction mixture was cooled to room temperature. The toluene layer was separated from the aqueous layer. The aqueous layer was extracted 1×50 mL toluene. The toluene extracts were combined, dried over magnesium sulfate, filtered and stripped under vacuum. The crude product was first purified by silica gel chromatography (5% ethyl acetate/methylene chloride). This crystallized from ethyl acetate—Hexane, yielding 3.4 g of product. This material was then dissolved in 75 mL of THF and was cooled to −78° C. To this cooled reaction mixture was added 6.05 mL of 1.6 M n-BuLi over a 5 min period. The mixture was then stirred for an additional 30 min at −78° C. This mixture was then quenched with 50 mL of water and was extracted 2×100 mL ethyl acetate. The ethyl acetate extracts were dried over magnesium sulfate filtered and stripped under vacuum. This material was again purified by silica gel chromatography (5% CH$_2$Cl$_2$ in ethyl acetate) followed by hexane recrystallizations. A total of 2.55 g of product was obtained.

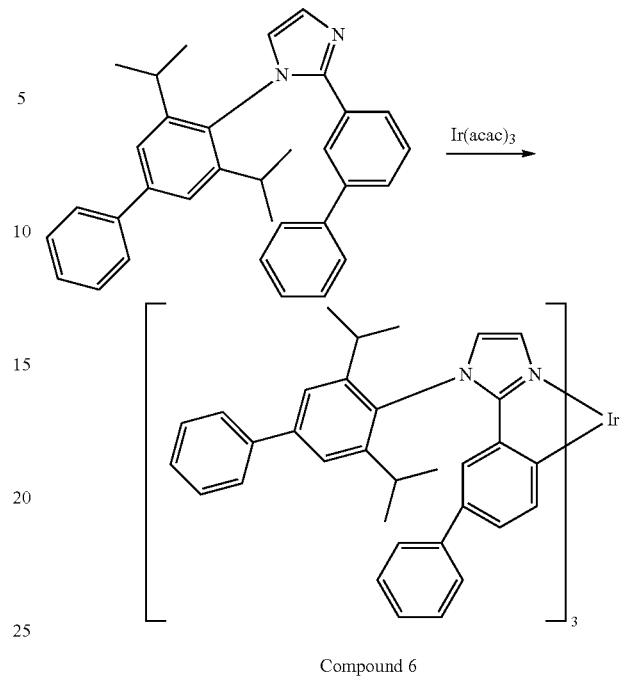

Compound 6

To a 50 mL Schlenk tube were added ligand (2.5 g, 5.48 mmol), tris(acetylacetonate) iridium (III) (0.539 g, 1.09 mmol, which was purified by an Al$_2$O$_3$ column with CH$_2$Cl$_2$ as eluent) and tridecane (50 drops). The mixture was degassed and heated in a sand bath (outside sand bath temperature was 255° C.) with stirring under a nitrogen atmosphere for 68 h. After cooling, the reaction mixture was dissolved with a mixture of solvent (CH$_2$Cl$_2$:Hexanes=1:1) and subjected to flash column chromatography. (SiO2; CH$_2$Cl$_2$:Hexanes=1:1). The solid after column chromatography was re-crystallized from a mixture of CH$_2$Cl$_2$ and methanol. The yield after crystallization was 1.46 g. (85% yield)

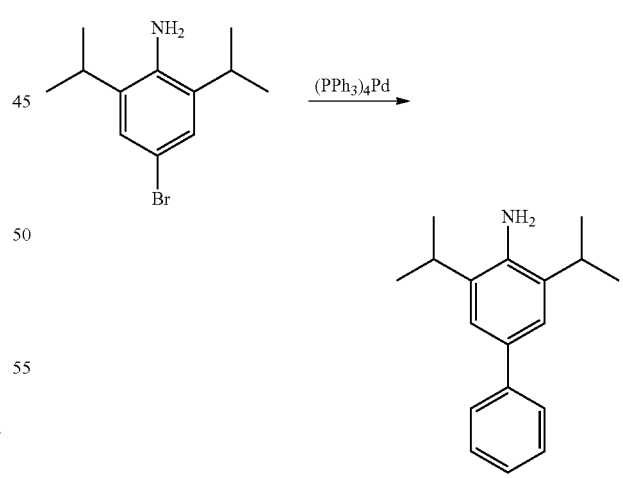

Example 7

Synthesis of Compound 7

Synthesis of 3,5-diisopropylbiphenyl-4-amine. 4-bromo-2,6-diisopropylaniline (16 g, 62.5 mmol), (PPh$_3$)$_4$Pd (2.2 g, 1.9 mmol), phenylboronic acid (11 g, 87.5 mmol), $K_3PO_4$ (26 g, 187 mmol), 400 mL of toluene and 40 mL of water were charged and heated up to reflux for overnight. The reaction mixture was purified by column and distillation method to give 9 g liquid (57% yield).

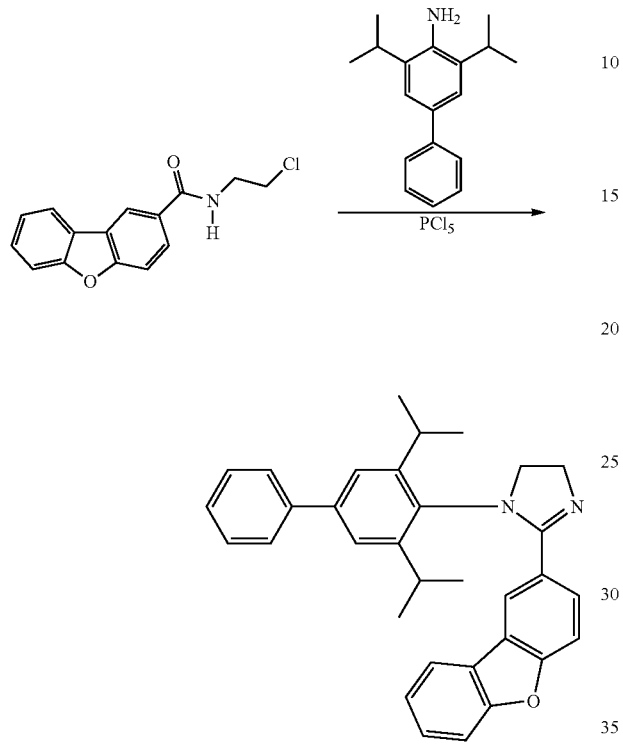

Synthesis of 2-dibenzofuran-1(3,5-diisopropylbiphenyl-4-yl)-4,5-dihydro-1H-imidazole A pre-dried 500 mL round bottomed flask was charged with N-(2-chloroethyl)dibenzofuran-2-carboxamide (5.6 g, 20.5 mmol) and m-xylene (150 mL) under nitrogen. Phosphorus pentachloride (7.1 g, 32.5 mmol) was then added to the solution. The reaction mixture was stirred and refluxed for 2 h under nitrogen. After the reaction mixture was cooled to ambient, 3,5-diisopropylbiphenyl-4-amine (5.7 g, 22.5 mmol) was added. The reaction was stirred and refluxed for 16 h. The flask was cooled to ambient and then placed in an ice-water bath to precipitate the product. The solid was filtered and collected, washed with cold toluene followed by hexanes. The product was added in 200 mL ethyl acetate and washed with 25% NaOH until the pH was between 8-10. The organic layer was washed with water, dried over sodium sulfate and the solvent was removed in vacuo to give 7.2 g (74% yield).

Synthesis of 2-dibenzofuran-1(3,5-diisopropylbiphenyl-4-yl)-1H-imidazole 2-dibenzofuran-1(3,5-diisopropylbiphenyl-4-yl)-4,5-dihydro-1H-imidazole (7.3 g, 15.5 mmol), 150 mL $CH_2Cl_2$ and acetonitrile (300 mL) were placed in a round bottomed flask. Potassium permanganate (4.9 g, 30. mmol) and Montmorillonite K-10 clay (10 g) were combined and grounded finely with a mortar and pestle and then added slowly and carefully to the solution. The mixture was stirred for 2 h. Methanol (40 ml) was then added to the reaction mixture to reduce the excess oxidant. The mixture was filtered through a short plug of Celite, and the solution concentrated in vacuo and separated in silica gel column eluting with 6% (v/v) ethyl acetate in $CH_2Cl_2$ to give 4.0 g (54%) product as a white solid.

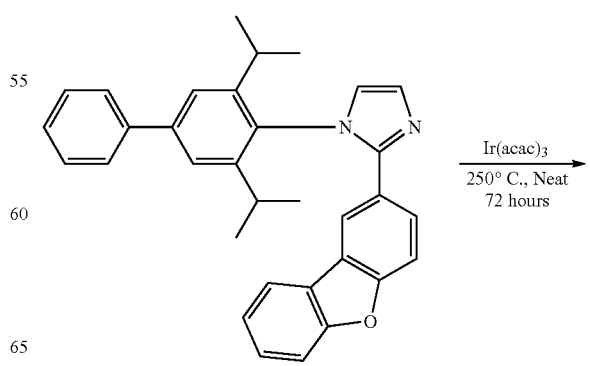

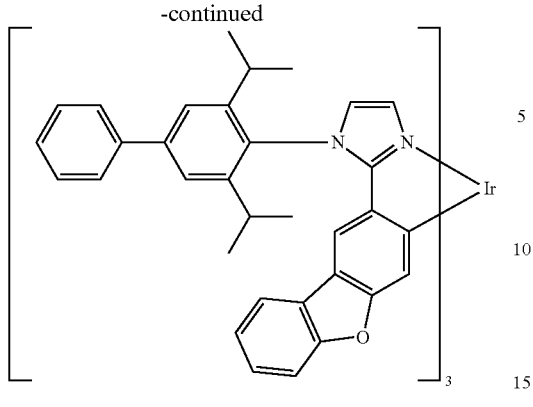

Compound 7

Synthesis of Compound 7

2-dibenzofuran-1(3,5-diisopropylbiphenyl-4-yl)-1H-imidazole 2 (2.5 g, 5.3 mmol), Ir(acac)$_3$ (0.592 g, 1.2 mmol) was charged in a reaction tube and heated up to 250° C. under nitrogen condition for 72 h. The reaction mixture was purified by silica gel column using 40% (v/v) CH$_2$Cl$_2$ in hexane as elute. About 1.5 g (79% yield) facial iridium complex was obtained.

Device Examples

All device examples were fabricated by high vacuum (<10$^{-7}$ Ton) thermal evaporation. The anode electrode is 800 Å of indium tin oxide (ITO). The cathode consisted of 10 Å of LiF followed by 1000 Å of Al. All devices were encapsulated with a glass lid sealed with an epoxy resin in a nitrogen glove box (<1 ppm of H$_2$O and O$_2$) immediately after fabrication, and a moisture getter was incorporated inside the package.

The organic stack of Device Examples 1-5 consisted of sequentially, from the ITO surface, 100 Å of Compound D as the hole injection layer (HIL), 300 Å of 4,4'-bis[N-(1-naphthyl)-N-phenylamino]biphenyl (α-NPD) as the hole transporting later (HTL), 300 Å of H1 or H2 doped with 15% of Compounds 1, 2, 3 or 5 as the emissive layer (EML), 50 Å of Host-1 as the ETL2, and 400 Å of Alq$_3$ (tris-8-hydroxyquinoline aluminum) as the ETL1.

Comparative example 1 was fabricated the same way as Device Example 1 except E1 was used the emitting dopant instead of Compound 1. Comparative example 2 was fabricated the same way as Device Example 1 except E2 was used the emitting dopant instead of Compound 1. Comparative example 3 was fabricated the same way as Device Example 5 except H3 was used the host instead of H1.

As used herein, the following compounds have the following structures:

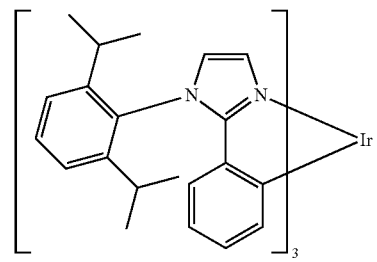
E1

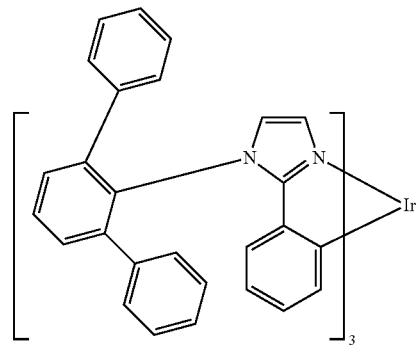
E2

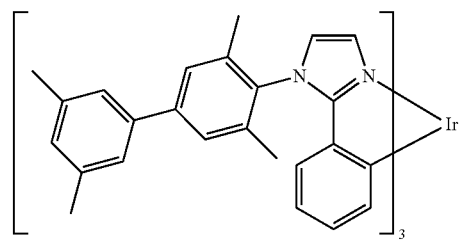
E3

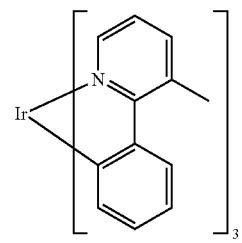
C1

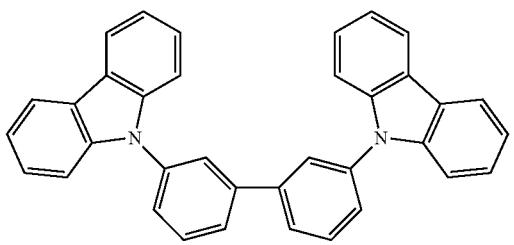
H3

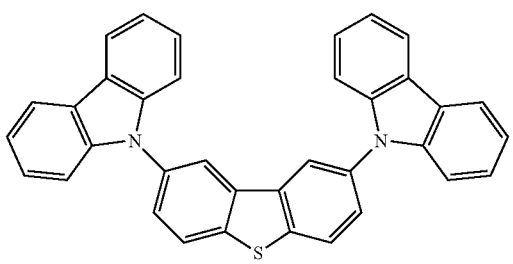
H1

H2

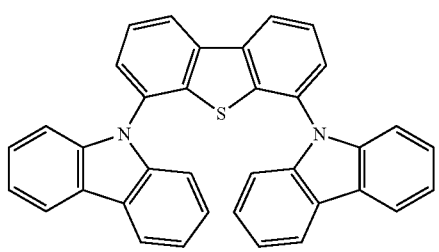

The device structures and data are summarized in Table 2 and Table 3. Table 2 shows the structure of devices containing emitting dopants doped in DBT containing hosts, and Table 3 shows the measured results for those devices.

TABLE 2

| Example | HIL | HTL | EML (300 Å, doping %) | | BL | ETL |
|---|---|---|---|---|---|---|
| Example 1 | C1 100 Å | NPD 300 Å | H1 | Compound 1 15% | H1 50 Å | Alq 400 Å |
| Example 2 | C1 100 Å | NPD 300 Å | H1 | Compound 2 15% | H1 50 Å | Alq 400 Å |
| Example 3 | C1 100 Å | NPD 300 Å | H1 | Compound 3 15% | H1 50 Å | Alq 400 Å |
| Example 4 | C1 100 Å | NPD 300 Å | H1 | Compound 5 15% | H1 50 Å | Alq 400 Å |
| Example 5 | C1 100 Å | NPD 300 Å | H2 | Compound 1 15% | H1 50 Å | Alq 400 Å |
| Comparative Example 1 | C1 100 Å | NPD 300 Å | H1 | E1 15% | H1 50 Å | Alq 400 Å |
| Comparative Example 2 | C1 100 Å | NPD 300 Å | H1 | E2 15% | H1 50 Å | Alq 400 Å |
| Comparative Example 3 | C1 100 Å | NPD 300 Å | H3 | Compound 1 15% | H1 50 Å | Alq 400 Å |

TABLE 3

| | 1931 CIE | | | FWHM | At 1000 cd/m² | | | | At 2000 cd/m² |
|---|---|---|---|---|---|---|---|---|---|
| | | | | | V | LE | EQE | PE | $LT_{80\%}$ |
| Example | x | y | $\lambda_{max}$ | (nm) | (V) | (Cd/A) | (%) | (lm/W) | (h) |
| Example 1 | 0.177 | 0.383 | 474 | 54 | 6.7 | 38.7 | 17.3 | 18.1 | 420 |
| Example 2 | 0.179 | 0.385 | 474 | 56 | 7.2 | 32.1 | 14.2 | 14.0 | 220 |
| Example 3 | 0.176 | 0.379 | 474 | 56 | 8.1 | 24.5 | 11 | 9.5 | 105 |
| Example 4 | 0.182 | 0.400 | 476 | 56 | 7.6 | 26.3 | 11.5 | 10.8 | 50 |
| Example 5 | 0.179 | 0.385 | 474 | 56 | 7.5 | 27.1 | 12 | 11.3 | 250 |
| Comparative Example 1 | 0.175 | 0.384 | 474 | 56 | 5.9 | 40.2 | 18.4 | 21.3 | 155 |
| Comparative Example 2 | 0.202 | 0.464 | 482 | 60 | 7 | 24 | 9.5 | 10.8 | 360 |
| Comparative Example 3 | 0.174 | 0.377 | 474 | 54 | 6.9 | 40.3 | 18.1 | 18.3 | 210 |

In Formula I, the Ar group is thought to increase the conjugation of C-ring. It is believed that this feature may increase lifetime compared to no Ar group. For example, Device Example 1 and Comparative Device Example 1 are the same except Device Example 1 uses Compound and Comparative Device Example 1 uses E1 as the emitting dopants respectively. Compound 1 and E1 are structurally similar except Compound 1 has a para-phenyl (para to the N) group attached to the C-ring. The device efficiencies are similar, but the device lifetimes are 420 h and 155 h respectively, at $LT_{80\%}$, starting at $L_0$=2000 cd/m². It may be advantageous to have at least one of the $R_1$ and $R_2$ substituents be a branched alkyl group, because the branched alkyl group may decrease intermolecular packing thereby leading to cleaner and/or lower temperature evaporation. For example, under a vacuum of about $10^{-7}$ Torr, Compound 2 sublimes at about 280° C. whereas E3 melted at 280° C. and evaporated with partial decomposition. It may also be advantageous to dope the emitting dopant in a dibenzothiophene containing host as the EML. For example, Device Example 1 and Comparative Device Example 3 are the same except Device Example 1 uses H1 while Comparative Device Example 3 uses H3 as the hosts respectively. The device efficiencies are similar, but the device lifetime are 420 h and 210 h respectively, at $LT_{80\%}$, starting at $L_0$=2000 cd/m². Device Example 5 (LT80%=250 h) with H2:Compound 1 as the EML is also more stable than Comparative Device Example 3.

As mentioned above, the Ar group in Formula I increases the conjugation of C-ring. Table 4 shows the 77 K PL excited state lifetime measurement in 2-methyltetrahydrofuran. Compounds 1, 2, 3 and 5 all have a para-phenyl group attached to the C-ring. Alternatively, E1 and E2 do not have an Ar group. The excited state lifetimes of Compounds 1, 2, 3 and 5 are 2.3-2.5 h whereas those of E1 and E2 are 3.2-3.3 h. It is believed a shorter excited state lifetime may lead to improved device stability.

TABLE 4

| Compound | 77K LT (μs) |
|---|---|
| Compound 1 | 2.5 |
| Compound 2 | 2.4 |
| Compound 3 | 2.5 |
| Compound 5 | 2.3 |
| E1 | 3.2 |
| E2 | 3.3 |

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore includes variations from the particular examples and preferred embodiments described herein, as will be apparent to one of skill in the art. It is understood that various theories as to why the invention works are not intended to be limiting.

The invention claimed is:

1. A first device comprising an organic light emitting device, comprising:
   an anode;
   a cathode; and
   an organic layer, disposed between the anode and the cathode, the organic layer comprising:
   Compound 1:

Compound 1

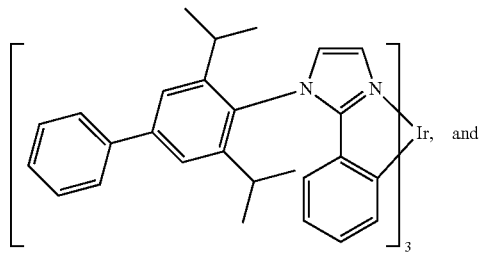

Compound H1

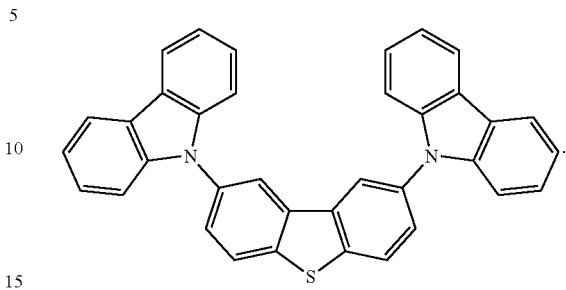

2. The device of claim 1, wherein the organic layer is an emissive layer and compound 1 is an emitting dopant and Compound H1 is a host material.

3. The device of claim 1, wherein the first device is a display.

4. The device of claim 1, wherein the first device is an organic light emitting device.

* * * * *